(12) United States Patent
Stanley

(10) Patent No.: US 9,417,203 B2
(45) Date of Patent: Aug. 16, 2016

(54) CONDUCTIVE LIQUID PROPERTY MEASUREMENT USING MULTIPLE CHARGE TRANSFER TIMES

(71) Applicant: Bourns, Inc., Riverside, CA (US)

(72) Inventor: James Gregory Stanley, Novi, MI (US)

(73) Assignee: BOURNS, INC., Riverside, CA (US)

( * ) Notice: Subject to any disclaimer, the term of this patent is extended or adjusted under 35 U.S.C. 154(b) by 2 days.

(21) Appl. No.: 14/559,706

(22) Filed: Dec. 3, 2014

(65) Prior Publication Data

US 2015/0160148 A1 Jun. 11, 2015

Related U.S. Application Data

(60) Provisional application No. 61/912,279, filed on Dec. 5, 2013.

(51) Int. Cl.
| | |
|---|---|
| *G01R 27/26* | (2006.01) |
| *G01N 27/22* | (2006.01) |
| *G01F 23/00* | (2006.01) |
| *G01F 11/00* | (2006.01) |
| *G01F 1/00* | (2006.01) |

(52) U.S. Cl.
CPC ............... *G01N 27/228* (2013.01); *G01F 1/00* (2013.01); *G01F 11/00* (2013.01); *G01F 23/00* (2013.01)

(58) Field of Classification Search
CPC ........... G01F 1/00; G01F 11/00; G01F 17/00; G01F 23/00
See application file for complete search history.

(56) References Cited

U.S. PATENT DOCUMENTS

| | | |
|---|---|---|
| 4,028,618 A | 6/1977 | Teass, Jr. |
| 4,309,660 A | 1/1982 | Stephen |
| 5,334,940 A | 8/1994 | Blades |

(Continued)

FOREIGN PATENT DOCUMENTS

| | | |
|---|---|---|
| EP | 1816448 | 8/2007 |
| WO | 2011073538 | 6/2011 |

OTHER PUBLICATIONS

International Search Report and Written Opinion of the International Searching Authority, received in International Patent Application No. PCT/US2014/068433, mailed Mar. 19, 2015 (11 pages).

(Continued)

*Primary Examiner* — Jermele M Hollington
*Assistant Examiner* — Temilade Rhodes-Vivour
(74) *Attorney, Agent, or Firm* — Michael Best & Friedrich LLP

(57) ABSTRACT

Systems and methods for making repeatable measurements of the dielectric constant and conductivity of a material, such as a liquid. In one example, a material property measurement system includes a measurement cell, a voltage measurement circuit, a capacitor, and a switch. The measurement cell is made of at least two conducting electrodes with liquid between the conducting electrodes. The switch is in a current path between the capacitor and the measurement cell. The capacitor is charged and then the switch is closed for a first time period and a first voltage measurement on the capacitor is performed. The capacitor is charged again and the switch is closed for a second time period and a second voltage measurement on the capacitor is performed. The two voltage measurements are used in a calculation to calculate a value related to capacitance between the at least two conducting electrodes of the measurement cell.

18 Claims, 14 Drawing Sheets

(56) References Cited

U.S. PATENT DOCUMENTS

| | | | |
|---|---|---|---|
| 5,519,323 A * | 5/1996 | Kordas | G01R 27/22 257/532 |
| 5,611,240 A * | 3/1997 | Yamaguchi | G01F 23/266 324/663 |
| 5,730,165 A | 3/1998 | Philipp | |
| 6,362,632 B1 * | 3/2002 | Livingston | G01F 23/266 324/629 |
| 6,577,112 B2 | 6/2003 | Lvovich et al. | |
| 6,690,173 B2 | 2/2004 | Blades | |
| 7,772,854 B2 | 8/2010 | Rezvani | |
| 2003/0057968 A1 * | 3/2003 | Wang | G01R 27/2605 324/690 |
| 2004/0051534 A1 | 3/2004 | Kobayashi et al. | |
| 2005/0172712 A1 * | 8/2005 | Nyce | G01F 23/268 73/304 C |
| 2009/0251126 A1 | 10/2009 | Ishino et al. | |
| 2010/0181180 A1 | 7/2010 | Peter | |
| 2010/0327884 A1 | 12/2010 | McCall et al. | |
| 2012/0182030 A1 * | 7/2012 | Calciolari | G01N 27/07 324/693 |
| 2012/0186334 A1 * | 7/2012 | Steinhauser | G01N 27/123 73/61.76 |

OTHER PUBLICATIONS

Philipp, H., "Charge Transfer Sensing Spread Spectrum Sensor Technology Blazes New Applications," Quantum Research Group Ltd., 1997 (9 pages).

BI-870 Dielectric Constant Meter, Brookhaven Instruments, downloaded <http://www.brookhaveninstruments.com/products/zeta_potential/p_ZP_BI-870.html> Dec. 3, 2013 (2 pages).

* cited by examiner

CONDUCTIVE LIQUID PROPERTY MEASUREMENT USING MULTIPLE CHARGE TRANSFER TIMES

RELATED APPLICATIONS

This application claims priority benefit to U.S. Provisional Application No. 61/912,279 filed Dec. 5, 2013, the entire contents of which are hereby incorporated by reference.

FIELD OF THE INVENTION

The present invention relates to systems and methods for making repeatable measurements of the dielectric constant and conductivity of a material. This measurement information may be used to identify when a material has an expected set of properties and to identify those electrical properties of the material.

BACKGROUND

Capacitive sensing, in general, is a known technology. For instance, a "theremin" is a musical instrument that effectively uses capacitive sensing to control the sound from a speaker. Additionally, capacitive sensors have been used in airplanes as fuel level sensors; in automobile applications for occupant classification; and in appliances as touch sensors, smart phones, and other consumer goods.

Prior art systems and methods are available to measure dielectric constant and conductivity of a material. However, such systems and methods are expensive, particularly for measuring liquids with fairly high conductivities. For example, instruments are available that can measure the dielectric constant of a liquid, but they impose limits on the liquid's conductivity to less than 10 µS/cm (e.g., see the BI-870 Dielectric Constant Meter produced by Brookhaven Instruments Corporation).

SUMMARY

Embodiments of the present invention provide measuring, with low cost sensors, the dielectric constant and conductivity of liquids that have relatively high conductivity (e.g., between 10 and 10,000 µS/cm). In another embodiment, high conductivity can include a material with a conductivity greater than 1000 µS/cm (e.g., between 1000 and 10,000 µS/cm). Embodiments of the invention are operable to make absolute capacitive measurements using sensors where a relatively low resistance (e.g., less than 100Ω) is placed directly across the capacitance to be measured.

An exemplary application of some embodiments of this invention is measuring quality of diesel exhaust fluid (DEF). DEF is used in a diesel engine after-treatment to reduce mono-nitrogen oxides (NOx) emissions from the engine's exhaust. However, embodiments of the invention are also applicable to other products that use or can benefit from a repeatable measure of the dielectric constant and conductivity of a liquid (or other material).

Embodiments of the invention also have additional application beyond absolute measurements of a material's dielectric constant and conductivity. For instance, embodiments of the invention could also be used as a capacitive sensor for other applications, especially when a conductive path is in parallel with the capacitance to be measured. For example, embodiments of the invention are applicable where a heating element is used as a capacitive sensor, such as occupant classification systems or steering wheel sensing systems, or where a capacitive sensing element is used in a conductive liquid, such as sea water.

Techniques used in some embodiments of the invention include: (a) using a resistor—capacitor (RC) time constant to measure a resistance or a capacitance at a sensor; (b) using a "charge transfer" technique such that switches and the voltage on a capacitor are used to measure a capacitance on a sensor; (c) using multiple charge transfer times to gain relative information about a material; and (d) discharging a capacitor into another capacitor and measuring the voltage on the discharged capacitor to calculate the capacitance on the second capacitor.

In one embodiment, the invention provides a liquid property measurement system including a measurement cell, a voltage measurement circuit, a capacitor, a first switch, and a second switch. The measurement cell is made of at least two conducting electrodes configured to receive a liquid between the conducting electrodes. The first switch and second switch are connected to the capacitor. The first switch is also in a current path between the capacitor and a voltage source. The second switch is also in a current path between the capacitor and the measurement cell. The first switch is closed to charge the capacitor and then opened. After the first switch is opened, the second switch is closed for a first time period. Then, the voltage on the capacitor is measured for a first voltage measurement. The first switch is then closed to charge the capacitor again and then opened. After the first switch is opened, the second switch is closed for a second time period. Then, the voltage on the capacitor is measured for a second voltage measurement. Using the two voltage measurements (i.e., the first voltage measurement and the second voltage measurement), a value is calculated related to the capacitance between at least two conducting electrodes of the measurement cell.

In another embodiment, the invention provides a material property measurement system (e.g., liquid property measurement system) including a measurement cell, a voltage measurement circuit, a capacitor, and a switch. The measurement cell is made of at least two conducting electrodes with liquid between the conducting electrodes. The switch is connected to the capacitor and is in a current path between the capacitor and the measurement cell. The capacitor is charged and then the switch is closed for a first time period. Then, a first voltage measurement on the capacitor is performed. The capacitor is charged again and the switch is closed for a second time period. Then, a second voltage measurement on the capacitor is performed. The two voltage measurements are used in a calculation to calculate a value related to capacitance between at least two conducting electrodes of the measurement cell.

In another embodiment, the invention provides a sensor for measuring the capacitance between two conductors when a resistance is in parallel with the capacitance. The sensor includes two conductors, a voltage measurement circuit, a capacitor, and a switch connected to the capacitor. The switch is located in the current path between the capacitor and one of the conductors. The capacitor is charged and then the switch is closed for a first time period. Then, a first voltage measurement on the capacitor is performed. The capacitor is charged again and the switch is closed for a second time period. Then, a second voltage measurement on the capacitor is performed. The two voltage measurements are used in a calculation to calculate a value related to capacitance between the two conductors.

In another embodiment, the invention provides a method of measuring a property of a liquid using a liquid property measurement system. The method includes receiving the liquid between at least two conducting electrodes. A capacitor is charged a first time. A switch connected to the capacitor is closed for a first time period to at least partially discharge the capacitor. Voltage on the capacitor is measured to determine a first voltage. The switch is located on a current path between the capacitor and at least two conducting electrodes. The method further includes charging the capacitor a second time. The switch connected to the capacitor is closed for a second time period to at least partially discharge the capacitor. The voltage on the capacitor is measured to determine a second voltage. A value is calculated related to an impedance between at least two conducting electrodes using the first and second voltage.

In some embodiments, the calculated value may be the dielectric constant and/or the conductivity of the liquid. Charging the capacitor can be accomplished by temporarily closing a first switch to connect to the capacitor to a power source. The at least two conductors can be part of a measurement cell. The second time period can be longer or shorter than the first time period.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
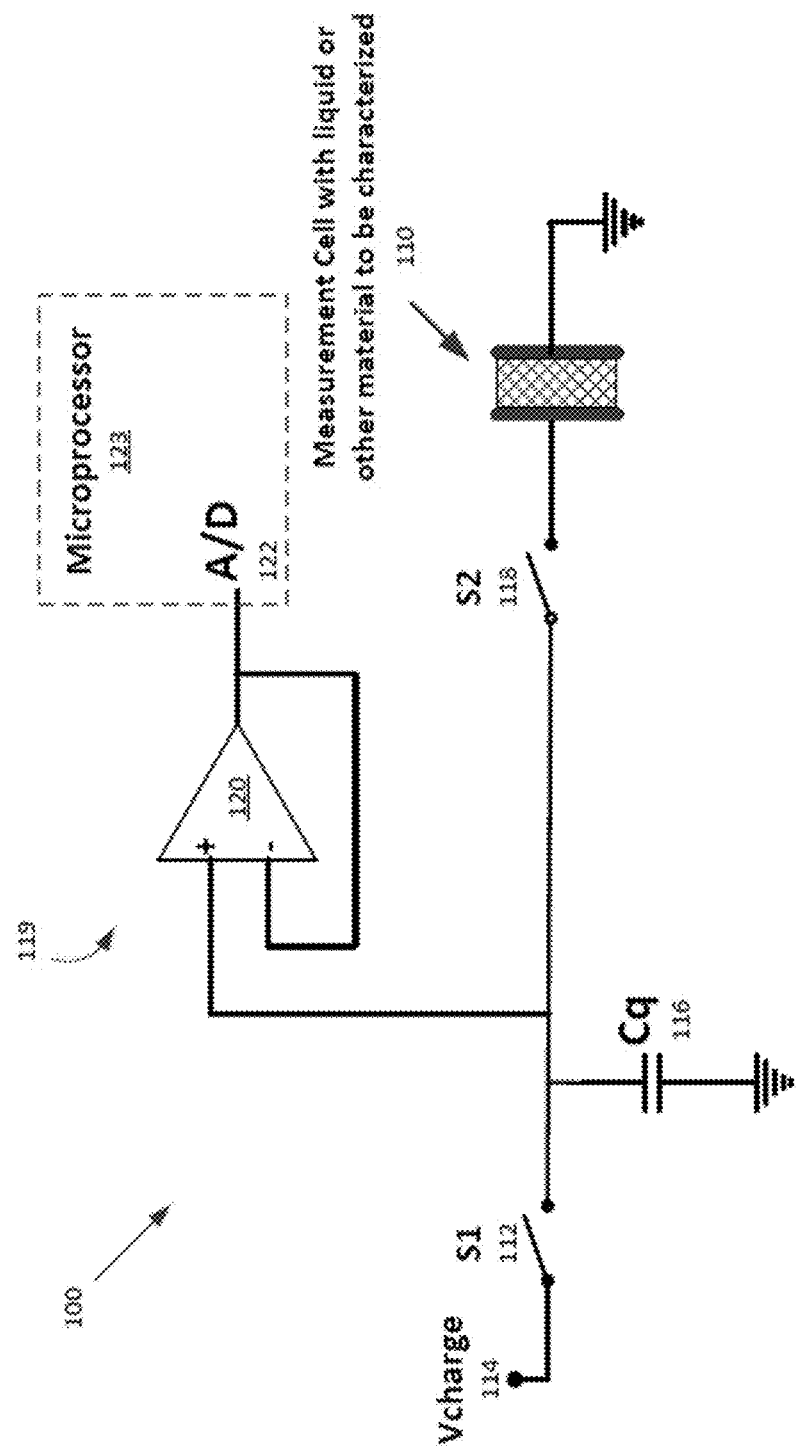
FIG. 1 illustrates a capacitive sensor system in accordance with embodiments of the invention.

FIG. 1 illustrates an embodiment of the capacitive sensory system 100. The capacitive sensory system 100 includes measurement cell 110 (or sensor), a charging switch or first switch (S1) 112, a power source or voltage source (Vcharge) 114, a charging capacitor (Cq) 116, a discharge switch or a second switch (S2) 118, and a voltage measurement circuit 119 that includes an operational amplifier (op amp) 120 and an analog-to-digital (A/D) converter 122. The measurement cell 110 includes at least two conducting electrodes configured to receive a liquid or other material to be characterized between the conducting electrodes. The measurement cell 110 is coupled to the charging capacitor 116 (i.e., capacitor) via the second switch 118. A first terminal of the measurement cell 110 is coupled to a second terminal of the second switch 118, and a second terminal of the measurement cell 110 is coupled to a common voltage connection (e.g., ground voltage). A first terminal of the capacitor 116 is coupled to a first terminal of the second switch 118, and a second terminal of the capacitor 116 is coupled to a common voltage connection. A first terminal of the first switch 112 is coupled to the first terminal of the capacitor 116. A positive input of the op amp 120 is coupled to the output of the capacitor 116, and a negative input of the op amp 120 is coupled to an output of the op amp 120 as feedback line. The output of the op amp 120 is coupled to the A/D converter 122 to convert an analog output of the operational amplifier into a digital signal. The A/D converter 122 is part of or coupled to a microprocessor. For instance, in FIG. 1, the A/D converter 122 is part of a microprocessor 123. The digital output of the A/D converter 122 is used by the microprocessor 123.

The capacitive sensory system 100 has the following measurement sequence. First, S2 118 is opened. Then, S1 112 is closed, which charges the capacitor Cq 116 until Cq 116 has a voltage of Vcharge 114. Next, S1 is opened, and a measurement of the voltage on Cq 116 is made using the A/D converter 122 of a microprocessor. S2 118 is closed for a short "charge transfer time," such as 100 nanoseconds (ns). Then S2 118 is opened. Another measurement of the voltage on Cq 116 is made using the A/D converter 122 of a microprocessor with both S1 112 and S2 118 opened.

The process of opening S2 118, closing S1 112, opening S1 112, measuring the voltage on Cq 116, closing S2 118, opening S2 118, and measuring the voltage again on Cq 116 is repeated again, except in the second process a relatively larger charge transfer time is used, such as 200 ns.

The measurements are used by the microprocessor 123 to calculate: a) an RC time constant, b) the actual charge sent through S2 118 during the initial few nanoseconds after S2 118 was closed, c) the capacitance of the measurement cell 110, and d) the resistance across the measurement cell 110.

The switches S1 112 and S2 118 (and other switches described) are electronic switches, such as field effect transistors (e.g., junction gate field-effect transistor (JFET) or metal-oxide-semiconductor field-effect transistor (MOSFET)), but other transistors may also be used. The switches S1 112 and S2 118 are controlled with software or hardware. For example, the switches 112 and 118 may be controlled directly by the microprocessor 123. Alternatively, the control the switches 112 and 118 can be part of an electronic circuit that is triggered by an edge of a signal generated from the microprocessor 123. Those skilled in the art of control of switches recognize that many possible methods can be used to control the switches and make the relevant measurements.

Figure 2:
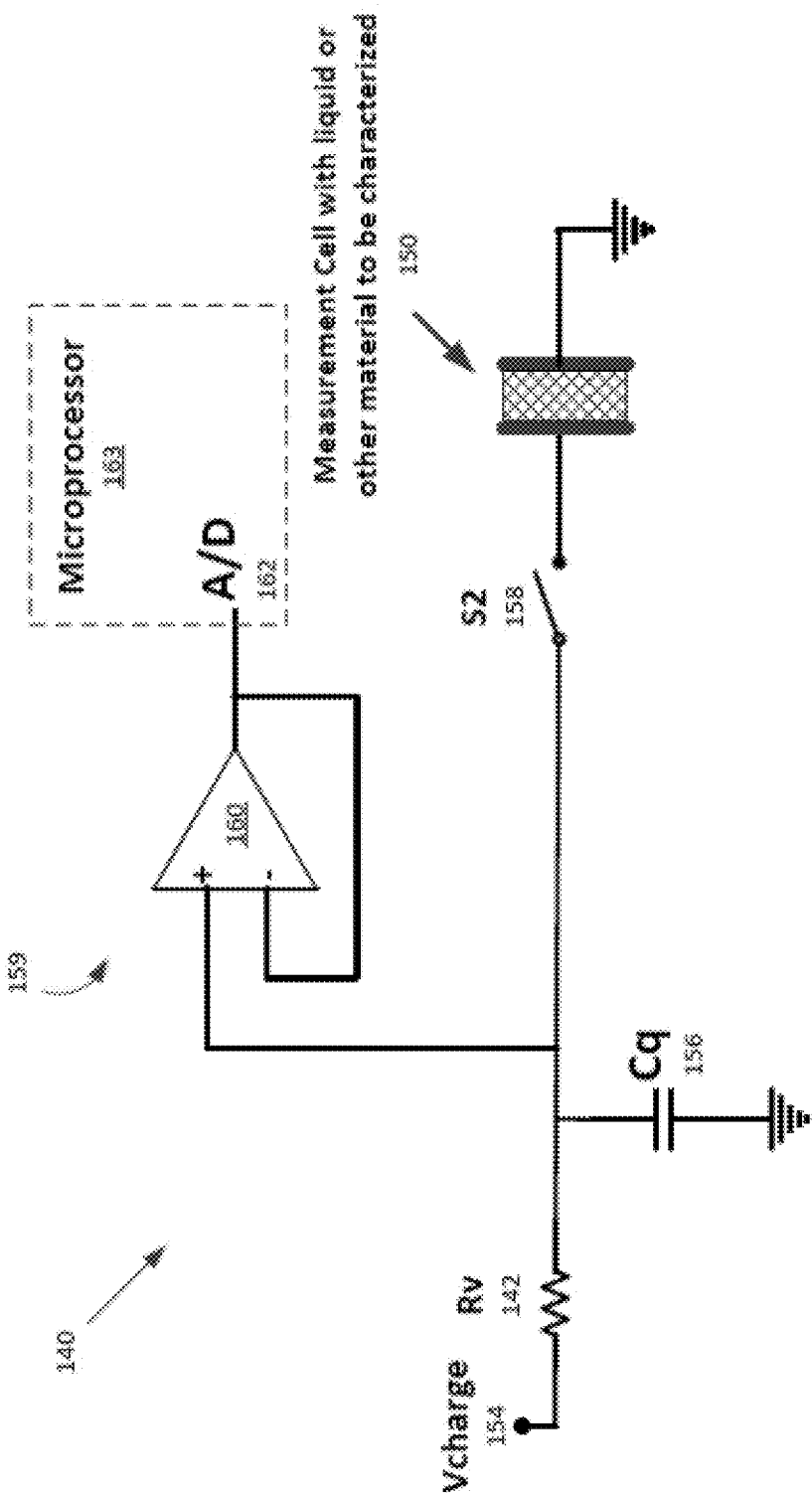
FIG. 2 illustrates a capacitive sensor system with a charging resistor.

FIG. 2 illustrates an alternative capacitive sensory system 140 using reference a charging resistor Rv 142 instead of charging switch S1. Similar to FIG. 1, the capacitive sensory system 140 includes a measurement cell 150, a power source or voltage source (Vcharge) 154, a charging capacitor (Cq) 156, a second switch (S2) 158, and a voltage measurement circuit 159 that includes an op amp 160, an A/D converter 162 that is part of a microprocessor 163. Since there is no switch S1, the capacitor Cq 156 is charged through the resistor Rv 142 that couples Cq 156 to the voltage source 154. As long as the value of Rv 142 is much greater than (e.g. at least 100 times greater) the largest resistance value of the measurement cell 150, the system 140 can operate with accurate measurements without a switch S1. Since Rv 142 provide a slower charge, enough time would need to elapse between switch S2 158 closures for Cq 156 to fully charge.

Figure 3:
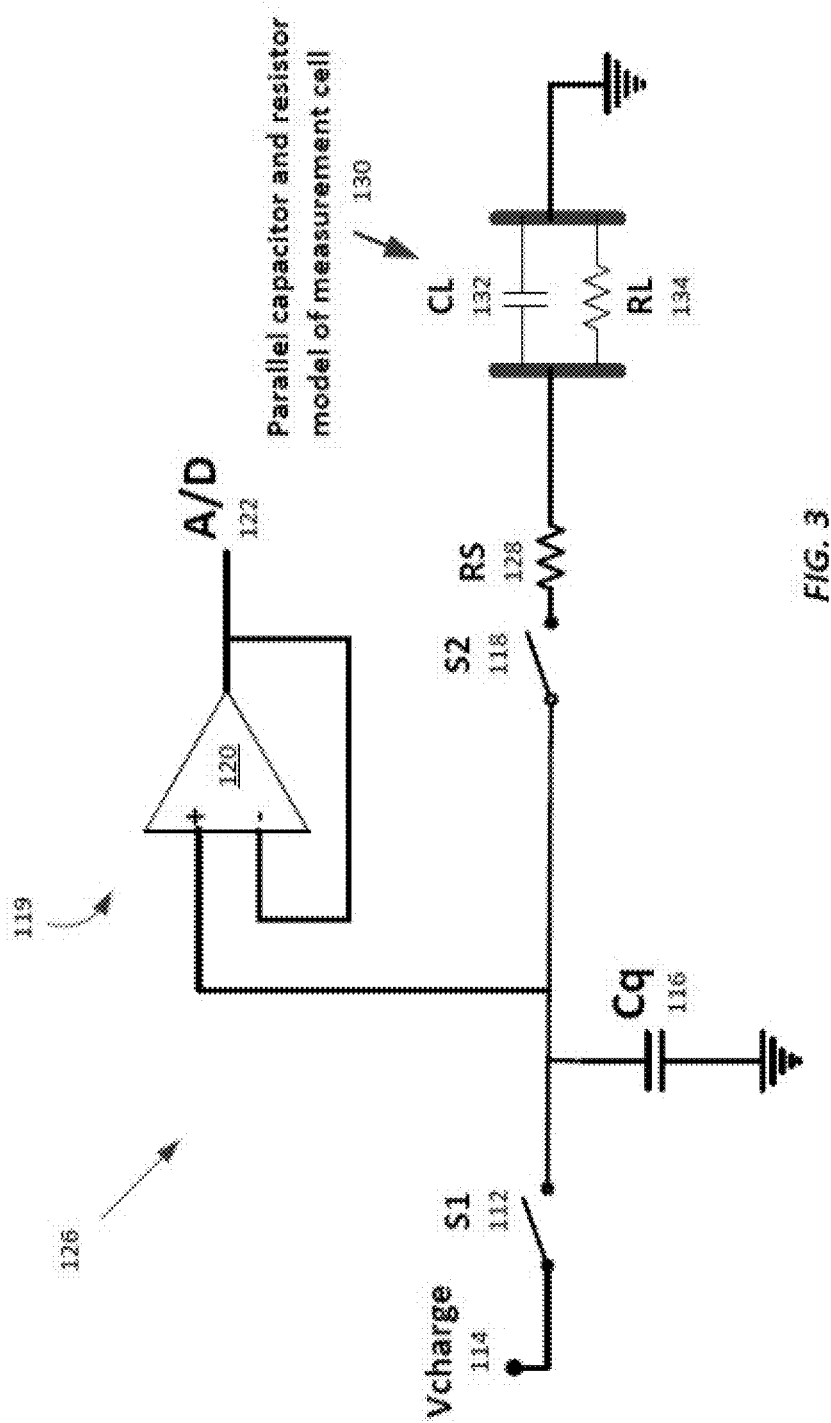
FIG. 3 illustrates the sensor system of FIG. 1 with equivalent load model.

FIG. 3 illustrates a block diagram of the equivalent circuit 126 of the measurement cell 130 and other components (e.g., S2 118) of the system 100 of FIG. 1. S2 118 and the traces used to couple Cq 116 to the measurement cell 130 via S2 are represented as a switch resistor (RS) 128 in series with the switch S2 118. RS 128 is the sum of the inherent resistance of switch S2 118 and any actual resistance added to the circuit, such as the traces connecting circuit components.

The measurement cell 130 is represented with a simplified equivalent electrical model that shows two parallel plates connected with a capacitor (CL) 132 and a resistor (RL) 134 between the plates. The capacitance between the plates (CL) 132 is referred to as plate capacitance, sensor capacitance, or sensing capacitor (CL) 132. The value of CL 132 depends upon the geometry and spacing of the plates and the dielectric of the material between the plates. In a similar way, the resistance between the plates (RL) 134, referred to as plate resistance, sensor resistance, or sensing resistor (RL) 134, depends upon the geometry and spacing between the plates, and the conductivity of the material.

The simplified equivalent electrical model 126 can illustrate the difficulty of measuring the properties of the material using other measurement techniques. A system that attempts to make a continuous wave current measurement through the measurement cell would need to separate the capacitive impedance from the resistive impedance. Such measurements can be performed with good signal-to-noise ratio, when the frequency of the signal sent through the cell (e.g., measurement cell) is high enough such that the resistive impedance is similar in magnitude to the capacitive impedance (e.g., the capacitive impedance $Z_C$ is not more than 10 times the resistive impedance $Z_R=R$, where $Z_C=(j\omega C)^{-1}$, R is the resistance, C is the capacitance, w is the angular frequency, and j represents the imaginary axis). For situations where the capacitance may be less than 10 pF and the resistance may be lower than 100 ohms, the frequency may need to be greater than 100 Megahertz (MHz). A high frequency is not preferred for a low-cost system.

The representation of the system 100 of FIG. 1 simplifies measurements and calculates the capacitance CL 132 and resistance RL 134 across the measurement cell 110 and 130 directly. The capacitance 132 and the resistance 134 can then be used to identify the dielectric constant and conductivity of the liquid (or other material).

Figure 4:
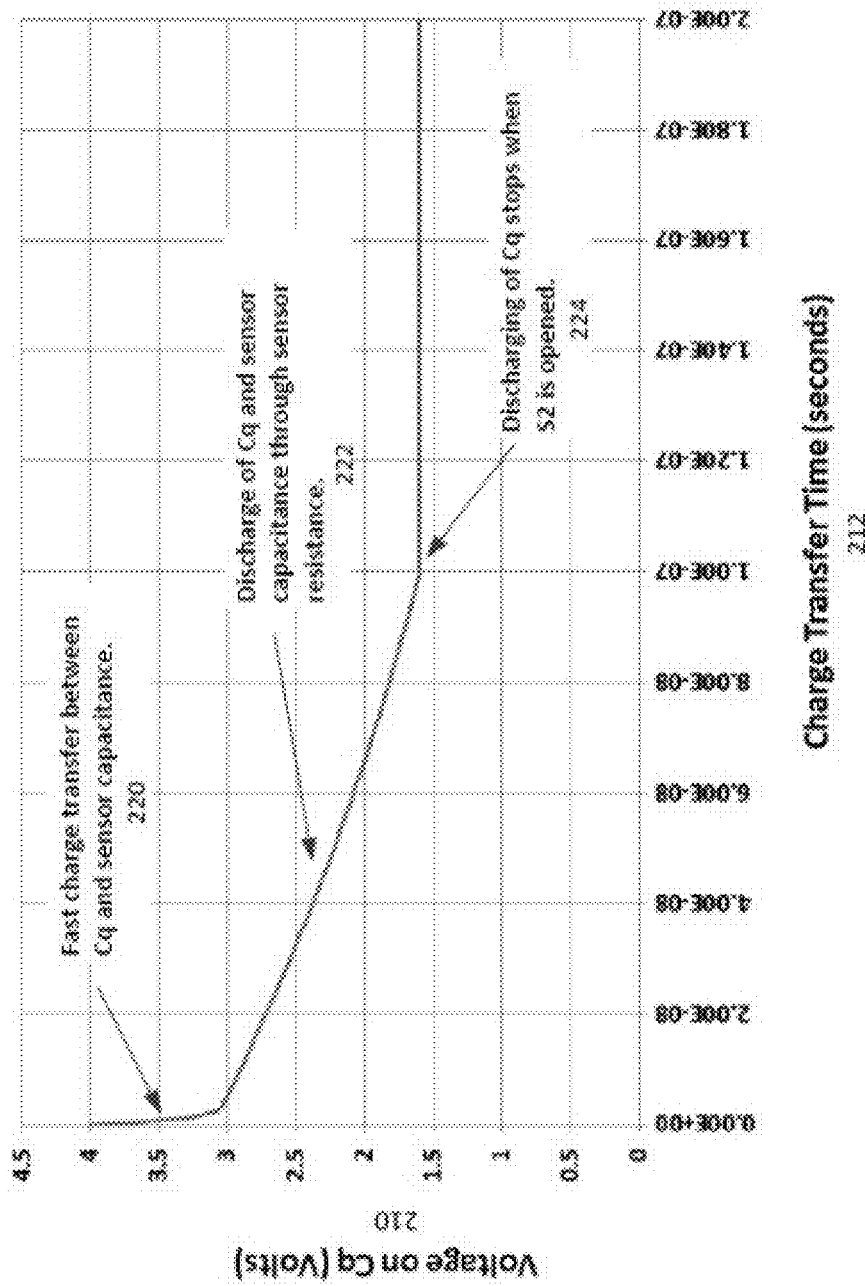
FIG. 4 illustrates a diagram of the voltage discharge by a capacitor over 100 nanosecond closure of a second switch.

FIG. 4 shows voltage 210 on the capacitor Cq (in Volts (V)) as a function of time (charge transfer time) 212 (in seconds) after the switch S2 is initially closed and then opened after 100 ns.

In this case, Vcharge equals 4 volts. The capacitance value for Cq is similar, or greater than, the expected capacitance value CL. The voltage on Cq drops quickly, as indicated by arrow 220, as the charge on Cq is shared with the sensing capacitor CL. The time required for this initial voltage drop depends on the resistance RS between Cq and the sensing capacitor CL and the value of the sensing capacitance CL itself, but this time can easily be much less than 10 ns. After that, the voltage on Cq starts falling more slowly because the sensing resistance RL is discharging the capacitors Cq and CL, as indicated by arrow 222. Once S2 is opened again 224 (i.e., 100 ns after S2 is initially closed), as indicated by arrow 224, the voltage on Cq stays relatively constant since the circuit does not have a significant resistance to discharge Cq. The voltage on Cq is measured sometime after S2 is opened (i.e., V100 or $V_{t=100\ ns}$). The exact time of the measurement after S2 is opened is not critical as the voltage on Cq is not changing significantly. For example, the sampling time may be 10 microseconds (μs) or 10 milliseconds (ms) after S2 is opened.

The fast drop 220 in the voltage on Cq during the first few nanoseconds, as indicated by arrow 220, contains the information about the capacitance CL. The slower drop in the voltage on Cq during the rest of the 100 ns duration, as indicated by arrow 222, is dependent on RL. One measurement before S2 is closed and one measurement after S2 is open (indicated by arrow 224), however, is not enough information to calculate CL and RL. A second sequence of measurements is used that repeats the same process but with S2 being closed for 200 ns instead of 100 ns.

Figure 5:
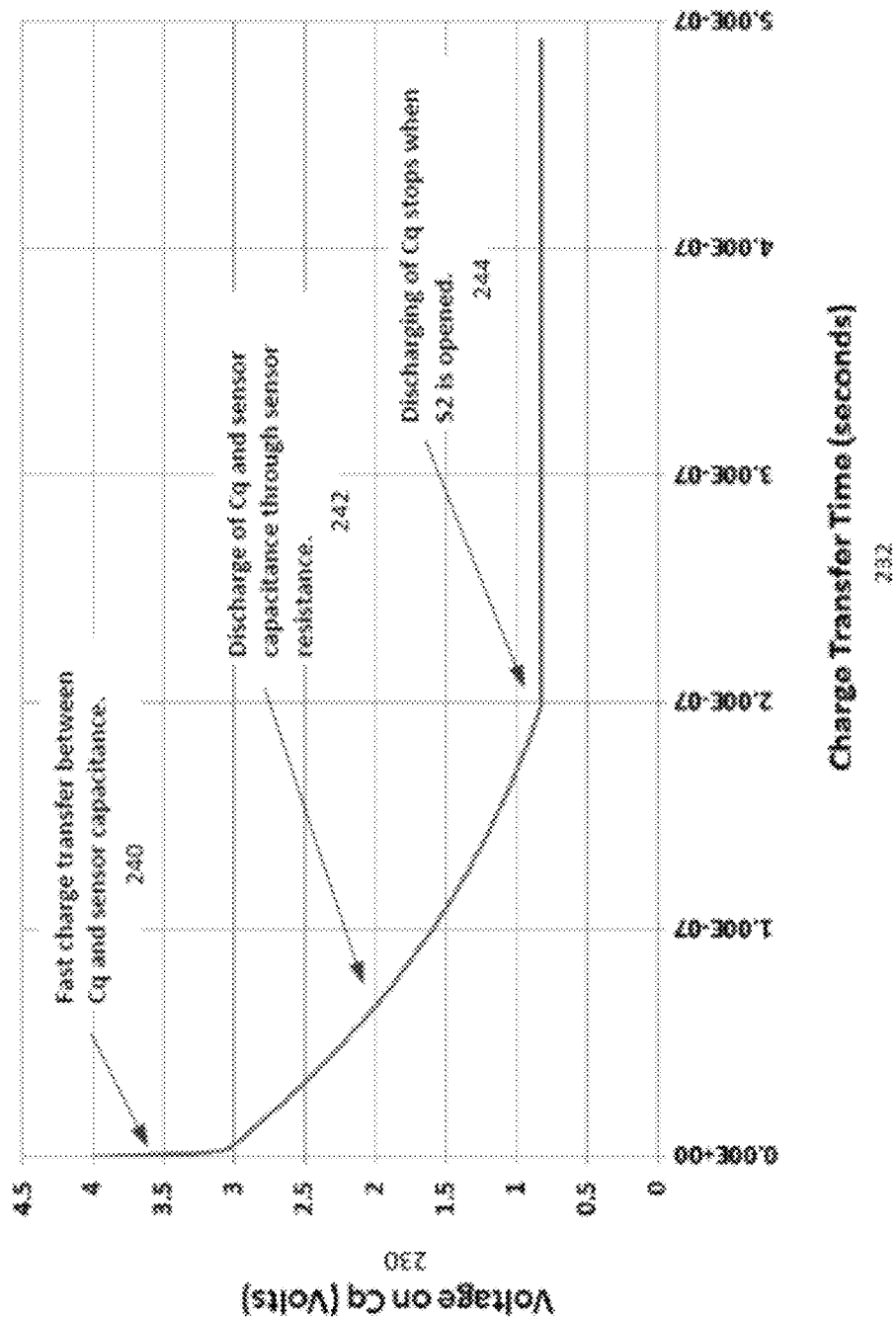
FIG. 5 illustrates a diagram of the voltage discharge by a capacitor over 200 nanosecond closure of the second switch.

The diagram of FIG. 5 shows the voltage 230 on Cq as a function of time (charge transfer time) 232 after the switch S2 is closed for 200 ns. The curve is the same for the first 100 ns with a sudden drop in voltage (indicated by arrow 240) and slower drop in voltage (indicated by arrow 242). This time, however, S2 is held closed for 200 ns and the voltage on Cq continues to fall. After 200 ns S2 is opened, as indicated by arrow 244, the voltage on Cq is measured (i.e., V200 or $V_{t=200\ ns}$).

Now the system has two measurements on a discharge curve, one at 100 ns (V100) and one at 200 ns (V200). Although voltage measurements at 100 ns and 200 ns are illustrated in this example, any two time periods may be used after the initial fast drop (220 of FIG. 4 or 240 of FIG. 5) in the voltage on Cq and before the complete discharge of Cq, which time period is represented by the slower drop (222 of FIG. 4 or 242 of FIG. 5) in the voltage on Cq on the discharge curve. The slower voltage drop on the discharge curve can be used to calculate the RC time constant of the measurement cell.

Referring back to the example with voltage measurements at 100 ns and 200 ns and assuming an exponential decay in the voltage, and the measurements at two known transfer times, the RC time constant can be determined using Equation 1, where Vout is the voltage at time t after S2 is closed; Vstart is the voltage at the time S2 is initially closed; exp( ) is an exponential function; R is the resistance of the circuit Cq, S2, and the measurement cell when S2 is closed; and C is the capacitance of the circuit Cq, S2, and the measurement cell when S2 is closed.

$$Vout=Vstart*\exp(-t/RC) \quad \text{[Equation 1]}$$

For the model shown FIG. 1, Equation 1 can be rewritten as Equation 2.

$$V200=V100*\exp(-t/RC) \quad \text{[Equation 2]}$$

The difference in times (t) is 100 ns. After inserting t, taking the natural log of both sides of the equation, and solving for RC, Equation 2 is represented as Equation 3.

$$RC=-(200\ ns-100\ ns)/\ln(V200/V100) \quad \text{[Equation 3]}$$

RC is determined by Equation 3. To find the voltage on Cq at any time (i.e., Vx or $V_{t=x}$), including the beginning of the transfer time (t0), Equation 3 can be rearranged and represented as Equation 4, where Vx represents the voltage at time tx.

$$Vx=V100/\exp(-(100\ ns-tx)/RC)) \quad \text{[Equation 4]}$$

The time for the fast charge transfer between Cq and the sensor capacitance CL (i.e., the fast drop in voltage, indicated by arrows 220 and 240) is dependent on the value of CL and the resistance RS. The initial drop in voltage can be estimated as occurring in five RC time constants. If the RS is 60 ohms (Ω) and CL is about 10 pF, then the time required for the fast charge transfer is approximately 3 ns (i.e., 5×RC=5× (60× 10e−12)=5×0.6 ns=3 ns). By estimating that the initial fast charge transfer time takes only 3 ns, the voltage after the charge sharing between the capacitors Cq and CL can be calculated as shown in Equation 5.

$$V3\ ns = V100/\exp(-(100\ ns - 3\ ns)/RC)) \quad \text{[Equation 5]}$$

Where V3 ns (i.e., $V_{t-3\ ns}$) is the voltage on Cq three nanoseconds after S2 is closed. Thus, without actually sampling at 3 ns after S2 was closed, the voltage on Cq at the time of the transition between the fast charge transfer 220 and 240 and the slow charge transfer 222 and 242 can be calculated. For simplicity of illustrating the calculations, 3 ns represents the time at which the voltage on Cq transitions between the fast charge transfer and the slow charge transfer.

The definition of capacitance states that C=Q/V, where charges on the plates are +Q and −Q respectively, and V is the voltage between the plates. Therefore, the definition of capacitance can be rewritten as Q=C*V. Since the voltage on Cq before and after the first 3 ns is known, the actual charge sent from Cq to CL can be calculated. Assuming the capacitance of Cq is known (which can be determined in the design), the charge transferred can be calculated and represented as Equation 6, where Qtransferred is the charge transferred from Cq to CL, V3 ns is the voltage of Cq at 3 ns after the transfer has begun, and Vbefore is the initial voltage on Cq before the charge transfer begins, and should be Vcharge (e.g., 4 V using FIGS. 4 and 5) in the example block diagrams shown in FIGS. 1 and 2.

$$Q\text{transferred} = Cq*V\text{before} - Cq*V3\ ns \quad \text{[Equation 6]}$$

Because Cq and CL are directly connected while S2 is closed, Cq and CL will have approximately the same voltage. Thus, the charge on CL and the voltage on CL after the first 3 ns of charge transfer can be calculated from Cq. Therefore, CL can be calculated and represented by Equation 7.

$$CL = Q\text{transferred}/V3\ ns \quad \text{[Equation 7]}$$

Once CL is known, RL can be calculated using Equation 8.

$$RL = RC/(Cq + CL) \quad \text{[Equation 8]}$$

Once CL and RL are calculated, knowledge of the measurement cell is then used to calculate the dielectric constant and conductivity of the material. For instance, a calibration with various materials is performed using a fixed measurement cell geometry. The result is used in a process to identify the absolute values of dielectric constant and conductivity. For example, a look-up table can be created that associates values for dielectric constant and conductivity with calculated values of CL and RL. In another example, values for dielectric constant and conductivity are calculated from the calculated values of CL and RL.

The description provided above uses, as an example, a system with transfer times of 100 ns and 200 ns, but other transfer times can be used to effectively sample the charge transfer and discharge curve at various times after the closure of S2 begins. The sampling of the curve is performed at times (e.g., after the fast charge transfer occurs), such that the voltage change on Cq due to the fast charge transfer to the sensing capacitance can be calculated. The sampling of the voltages after the fast charge transfer occurs is used to calculate the sensor capacitance CL. 100 ns and 200 ns transfer times were chosen as an example because these times are compatible with potential timing capabilities of low cost microprocessors. Smaller transfer times, such as 10 ns and 20 ns, can give better results, especially when the sensor resistance RL is very low. Appropriate charge transfer times are dependent on the measurement cell and the type of liquid being measured, and the charge transfer times might be orders of magnitude larger or smaller than the example described above.

The same measurement concept can be used by sampling the voltage on Cq every nanosecond (or faster) to measure the transfer and discharge curve directly and use an algorithm to calculate the equivalent circuit (capacitance, resistance, and series inductance) at the sensor cell. This alternative of more frequent sampling generally involves more complex and costly electronic hardware than the circuit shown in FIGS. 1 and 2.

Figure 6:
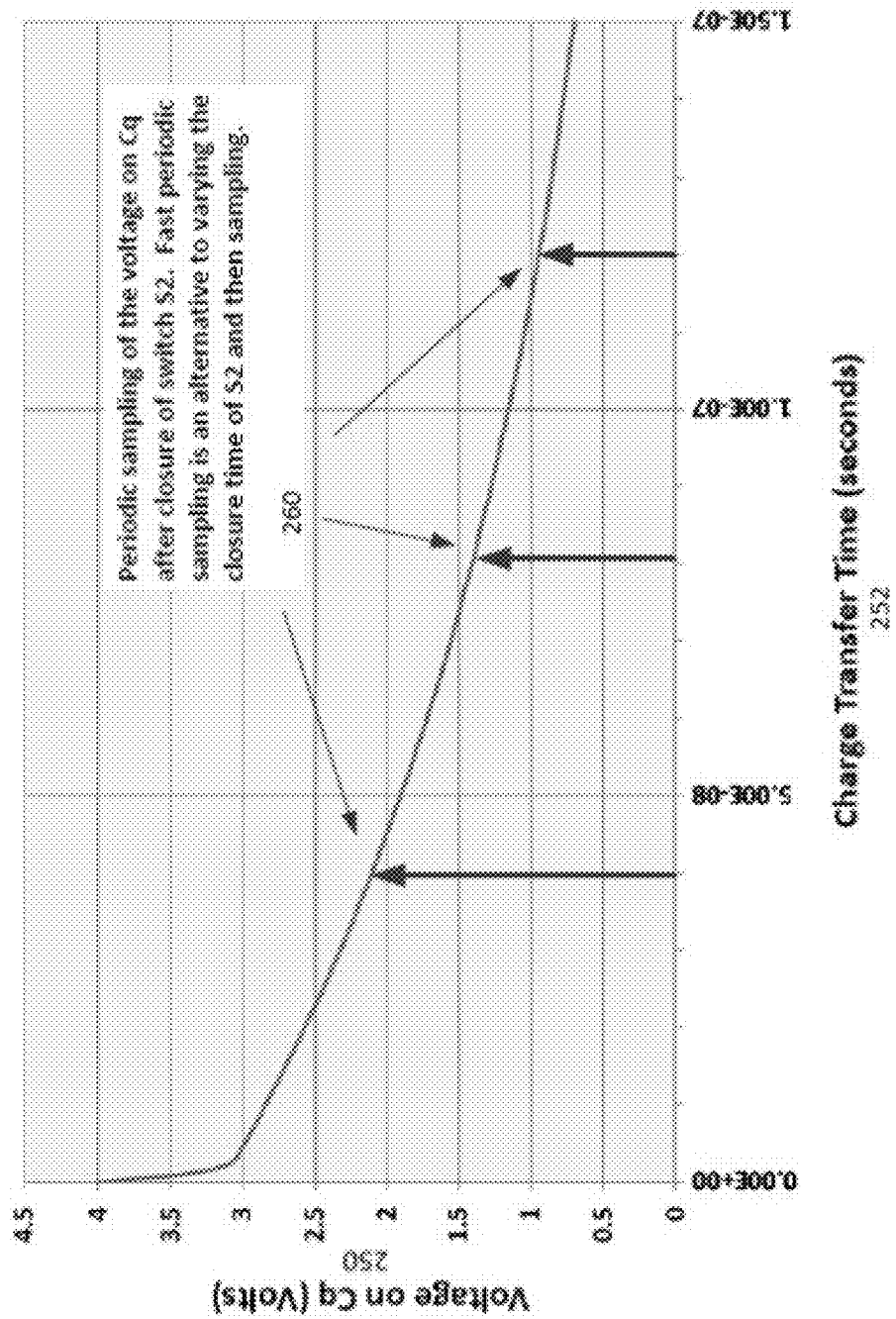
FIG. 6 illustrates a diagram of the voltage discharge by a capacitor after the closure of the second switch.

FIG. 6 shows the voltage 250 on Cq as a function of time (charge transfer time) 252 along with the sampling of that voltage 260 after the switch S2 is closed. Voltage sampling 260 occurs sometime (e.g., start 40 ns) after S2 is closed and continues to sample periodically (e.g., every 40 ns). Data from these samples could use the same calculations as previously described in Equations 1-8. But in this case, switch S2 remains closed until all of the voltage measurements (i.e., the samples) are taken. Fast periodic sampling (e.g., sampling with a periodicity of less than 100 ns) is an alternative to varying the closure time of the S2 (i.e., where S2 is closed once for a set of measurements) and then performing measurements.

The description and calculations above assume a near perfect charge transfer and discharge curve. In a real system, some inductance in the circuit, some parasitic capacitance in parallel with the sensor capacitance, and, as mentioned, resistance in series with the charge transfer path (between Cq and CL) may occur. These real system effects will create some error in the calculation of CL and RL because the simple calculations do not account for these real system effects. Factoring in for these real system effects would add complexity to the calculations and may require more complex and costly electronic hardware. In some instances, these real system effects or components are measured and a more complicated calculation to find CL and RL is used that takes these aspects into consideration. The increased accuracy may justify the increased complexity in some scenarios. Other variations of the exemplary algorithm may also create useful results and be desirable in certain scenarios.

This system 100 of FIG. 1 uses basic components to effectively sample the voltage on Cq 116 at very short time durations after S2 118 is closed. The system 100 of FIG. 1 then uses those samples to identify the charge transferred to Cq 116 and the voltage on the sensor capacitance after the "fast charge transfer," which may take as little as a nanosecond. The sensor capacitance can then be directly calculated, even though the sensor capacitance is in parallel with a low-valued resistance (i.e., sensor resistance).

The measurement concept of the system in FIG. 1 is based on the large difference between the RC time constant of the "fast charge transfer" and the RC time constant of the "discharge of Cq and the sensor capacitance through the sensor resistance," as illustrated in the curves shown in FIGS. 4-5. If, for one or more various reasons, these time constants are close to each other, the different sections of the curve are no longer as separable and the sensor capacitance may not be calculated accurately.

Figure 7:
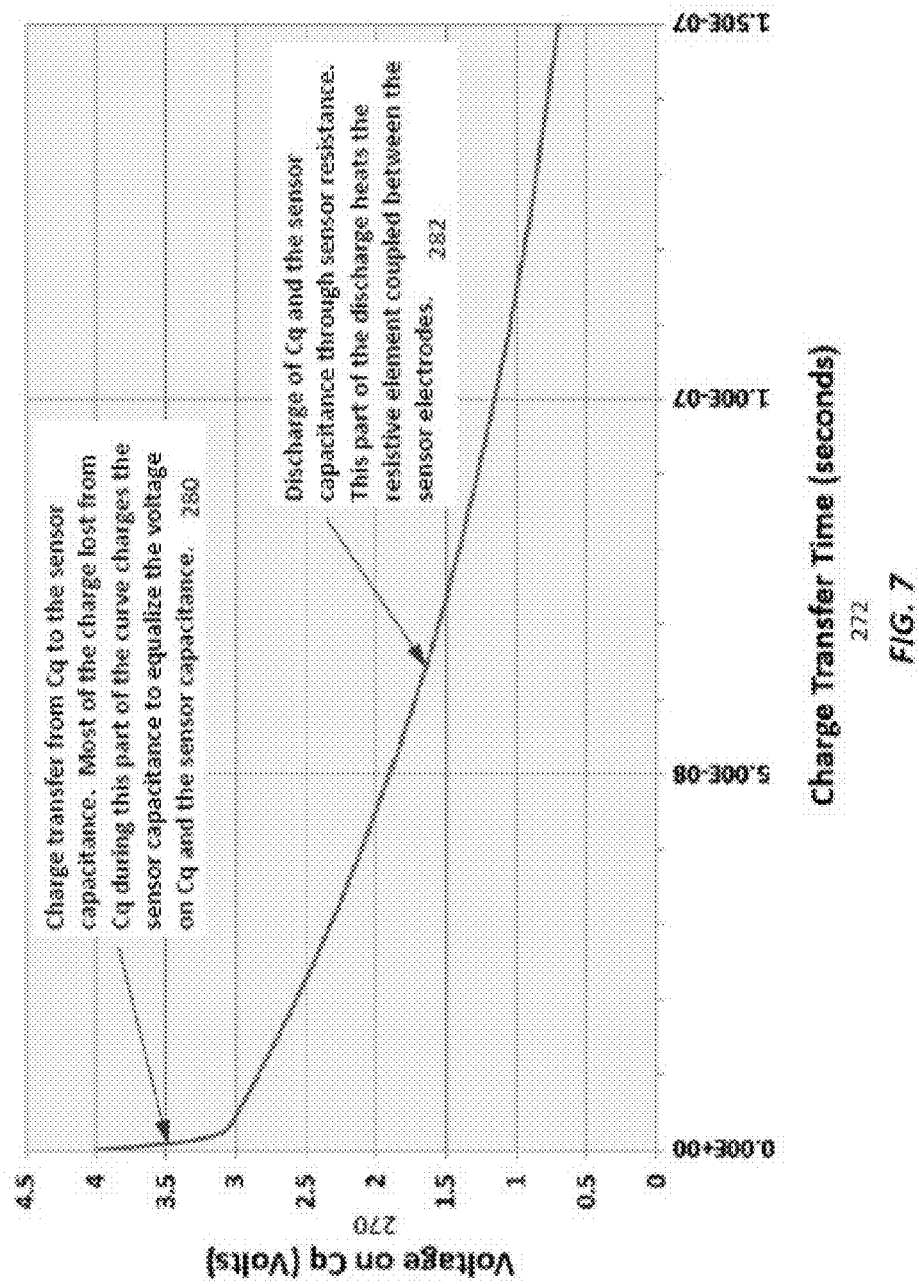
FIG. 7 illustrates a diagram of the voltage discharge by a capacitor after the closure of the second switch.

FIG. 7 shows the voltage 270 on Cq as a function of time (charge transfer time) 272 along with identifying different sections 280 and 282 of the discharge curve after the switch S2 is closed. The fast drop of the voltage 280 at the beginning of the curve is almost entirely from some of the charge on Cq moving to CL until the voltage level on the two capacitors are equal. The curve in FIG. 7 shows this occurring within several nanoseconds, but this fast drop could happen in less than 1 nanosecond, depending on the capacitance values of CL and the series resistance RS of switch S2. The slower decay of the voltage 282 is due to the current through the resistive element between the sensor electrodes. The current flowing during this slower decay of the voltage on Cq is heating the resistive elements RS and RL.

Fortunately, increasing the "gap" and decreasing the "area" of the sensor, when designing a measurement cell to be used with a highly conductive liquid, can be used to increase the difference between the "fast charge transfer" RC time constant and the "slow discharge" RC time constant. Decreasing the "area" of the sensor decreases the capacitance CL and increasing the "gap" increases the resistance RL, which combine to decrease the "fast charge transfer" time constant and increase the "discharge" time constant, allowing the different sections of the curve to be more separable. Thus, the sensor design is based on the conductivity of the intended liquid (or material) to be measured.

As might be expected, measuring the sensor capacitance CL when the sensor resistance RL is large is easier than when the sensor resistance RL is small. A large RL creates a large "discharge" time constant. At the extreme, to calculate CL when there is a "discharge" time constant in the milliseconds, the system can close S2 and make an A/D measurement 10 μs after the transfer time starts.

Accordingly, the system shown in FIGS. 1 and 2 can use simple controls and low cost hardware to calculate CL even when RL is low enough to cause the sensor capacitance CL to discharge very quickly.

Figure 8:
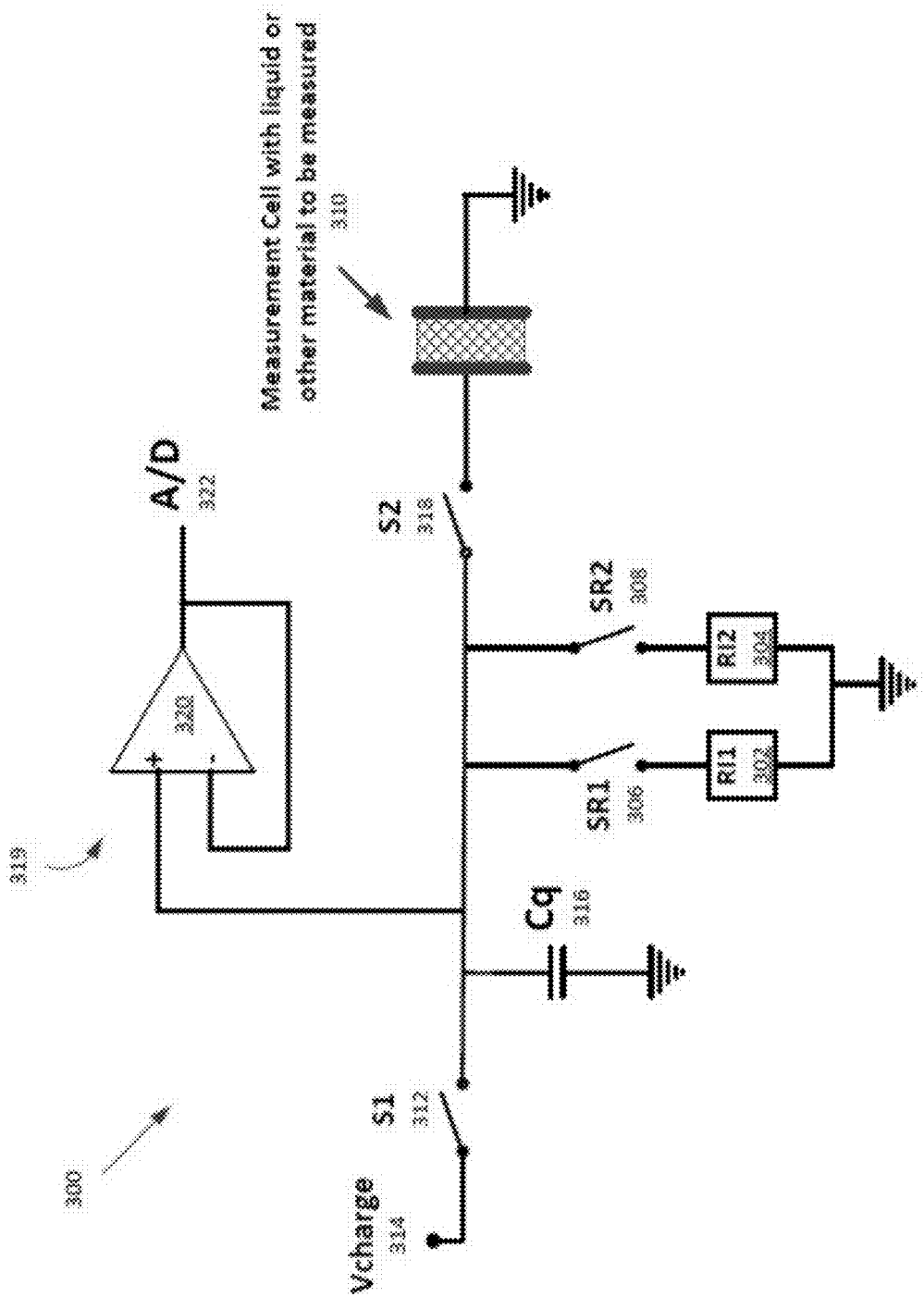
FIG. 8 illustrates another embodiment of the capacitive sensor using reference impedances.

FIG. 8 illustrates an alternative capacitive sensory system 300 using reference impedances 302 and 304. The reference impedances are labeled RI1 302 and RI2 304. The reference impedances (or reference impedance components) are real circuit components on the printed circuit board. The reference impedances are generally a capacitor (e.g., RI 302) in parallel with a resistor (e.g., RI 304) like the model of the measurement cell (130 shown in FIG. 3), but could include other circuit components (e.g., inductor) and configurations. The reference impedances 302 and 304 are connected to the voltage measurement circuit via additional charge transfer switches SR1 (a first reference switch) 306 and SR2 (a second reference switch) 308. The capacitive sensory system 300 of FIG. 8 also includes components and connections similar to the capacitive sensory system 100 shown and described in relation to FIG. 1. The capacitive sensory system includes a measurement cell 310, a first switch (S1) 312, a power source or voltage source (Vcharge) 314, a charging capacitor (Cq) 316, a second switch (S2) 318, and a voltage measurement circuit 319 that includes an op amp 320 and an A/D converter 322. A first terminal of the first reference switch (SR1) 306 is coupled to the first terminal of the capacitor Cq 316, a second terminal of the first reference switch (SR1) 306 is coupled to a first terminal of the first reference impedance (RI1) 302, and a second terminal of the first reference impedance (RI1) 302 is coupled to a common voltage connection. Similarly, a first terminal of the second reference switch (SR2) 308 is coupled to the first terminal of the capacitor Cq 316, a second terminal of the second reference switch (SR2) 308 is coupled to a first terminal of the second reference impedance (RI2) 304, and a second terminal of the second reference impedance (RI2) 304 is coupled to a common voltage connection.

The same measurement sequence as described above in relation to FIGS. 1-2 may be used, but the measurement sequence performs the charge transfer with one of the reference impedances 302 and 304 in place of the measurement cell 310. For example, instead of closing S2 318 for the transfer times, the system closes SR1 306 for the transfer times to measure RI1 302, and the system closes SR2 308 for the transfer times to measure RI2 304.

For instance, the system 300 can use the following measurement sequence for RI1 302, then RI2 304, then the measurement cell 310. First, S2 318, SR1 306, and SR2 308 are opened. Then, S1 312 is closed, which charges the capacitor Cq 316 until Cq 316 has a voltage of Vcharge 314. Next, S1 312 is opened, and a measurement of the voltage on Cq 316 is made using the A/D converter 322 of a microprocessor. SR1 306 is closed for a short "charge transfer time," such as 100 ns. Then SR1 306 is opened. Another measurement of the voltage on Cq 316 is made using the A/D converter 322 of a microprocessor with S1 312, S2 318, SR1 306, and SR2 308 opened.

The process of opening SR1 306, closing S1 312, opening S1 312, measuring the voltage on Cq 316, closing SR1 306, opening SR1 306, and measuring the voltage again on Cq 316 is repeated again, except in the second sequence a relatively larger charge transfer time is used, such as 200 ns.

The process can be repeated again for measuring RI2 304 (using SR2 308) instead of RI1 302 (using SR1 306). The process begins with the opening SR2 308, closing S1 312, opening S1 312, measuring the voltage on Cq 316, closing SR2 308 for the short charge transfer time (e.g., 100 ns), opening SR2 308, and measuring the voltage again on Cq 316. The process of opening SR2 308, closing S1 312, opening S1 312, measuring the voltage on Cq 316, closing SR2 308, opening SR2 308, and measuring the voltage again on Cq 316 is repeated again, except in the second sequence a relatively larger charge transfer time is used, such as 200 ns.

Then, the process is repeated with the opening and closing of S2 318, as described in relation to the system 100 shown in FIG. 1. If the process is used to generate measurements for RI1 302, RI2 304, and the measurement cell 310, up to twelve different voltage measurements can be made (i.e., four voltage measurements for each of RI1 302, RI2 304, and the measurement cell 310; corresponding to six voltage measurements related to the short charge transfer time, and six voltage measurements related to the long charge transfer time).

The same Vcharge 314, Cq 316, signal buffer 320 (or op amp), and A/D converter 322 are used for the measurements. S2 318, SR1 306, and SR2 308 are similar switches and the printed circuit board layout traces going to the three switches are nearly identical. Making the actual circuits going to the measurement cell 310, RI1 302, and RI2 304 as similar as possible can improve the accuracy or precision of the measurements of the measurement cell 310. However, other embodiments may use one or more of different switches, different traces, and different measurement components.

The reference impedances 302 and 304 have known values of capacitance C and resistance R and can, therefore, be used as known absolute values (that do not need to be calculated). The measured values of the parallel resistance and capacitance of the measurement cell 310 can be compared to the results of the reference impedance measurements in a simple calculation to accurately calculate the final values for CL and RL. An example compensation calculation using the reference impedances is shown in Equation 9.

$$CL\ \text{final} = (CL - CR1) * (CR2A - CR1A)/(CR2 - CR1) + CR1A \quad \text{[Equation 9]}$$

Where: CLfinal is the final calculated value for the capacitance across the measurement cell, CL is the measured value of capacitance across the measurement cell, CR1 is the measured value of capacitance across reference impedance 1 (RI1), CR2 is the measured value of capacitance across reference impedance 2 (RI2), CR1A is the actual value of the capacitance across reference impedance 1, and CR2A is the actual value of the capacitance across reference impedance 2.

This kind of calculation shown in Equation 9 compensates for offset shifts and gain changes in the voltage measurement circuit (including variations in the absolute transfer times), as well as imperfections in the assumed shape of the transfer and discharge curve caused by unwanted parasitic capacitances, series inductances and resistances. Thus, using the reference impedance measurements can generate more precise final values for CL and R (also referred to as compensated values). If the capacitive sensory system 300 changes, the capacitive sensory system 300 will change for both the reference impedance measurements and the measurement cell measurements. If needed, additional reference impedances can be added and a similar compensation calculation can be performed for each range of sensing. The number reference impedances can use a different range of capacitors and resistors to increase the range of conductivity of liquids (or other materials) that can be measured.

Figure 9:
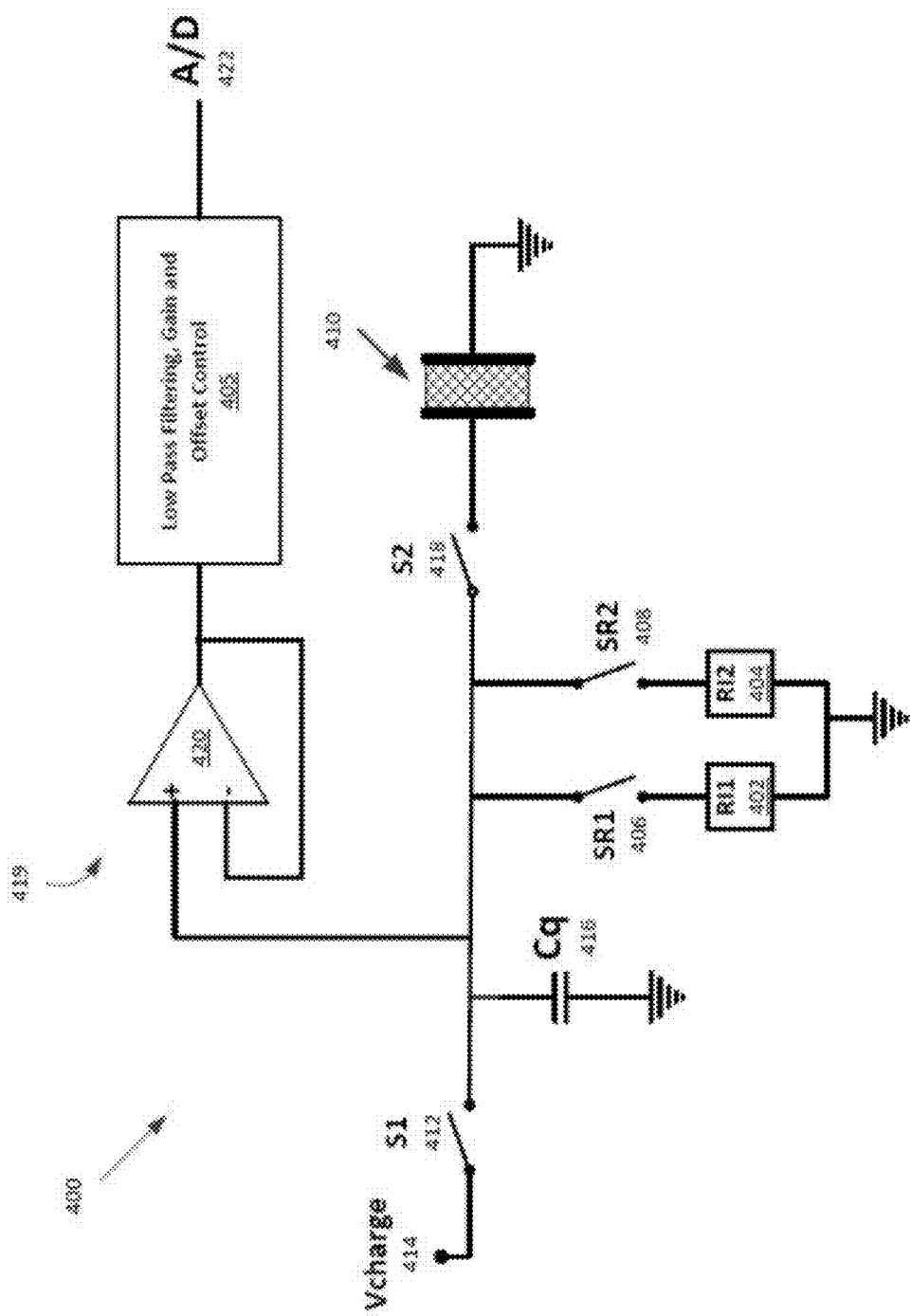
FIG. 9 illustrates another embodiment of the capacitive sensor system including a signal conditioning block.

For some applications, some signal conditioning of the measurement of the voltage on Cq may be used. Similar to FIG. 8, FIG. 9 illustrates a capacitive sensory system 400 using reference impedances RI1 402 and RI2 404, but also includes a low pass filter and/or gain and offset control 405 for signal conditioning. The low pass filtering, gain control, and/or offset control 405 may be referred to as a signal conditioning block or circuit. The reference impedances 402 and 404 are connected to the voltage measurement circuit via additional charge transfer switches SR1 406 and SR2 408. The capacitive sensory system 400 of FIG. 9 also includes components and connections similar to the capacitive sensory system 100 shown and described in relation to FIG. 1. The capacitive sensory system includes a measurement cell 410, a first switch (S1) 412, a power source or voltage source (Vcharge) 414, a charging capacitor (Cq) 416, a second switch (S2) 418, and a voltage measurement circuit 419 that includes an op amp 420, a signal conditioning block 405, and an A/D converter 422.

The signal conditioning block 405 can be a passive low pass filter or include more complex gain and offset control circuitry. One of skill in the art of basic signal conditioning will recognize that there are many options to provide signal conditioning. A similar signal conditioning block can be added at the output of the A/D converter 422 (instead of the input of the A/D converter 422) in other embodiments.

Figure 10:
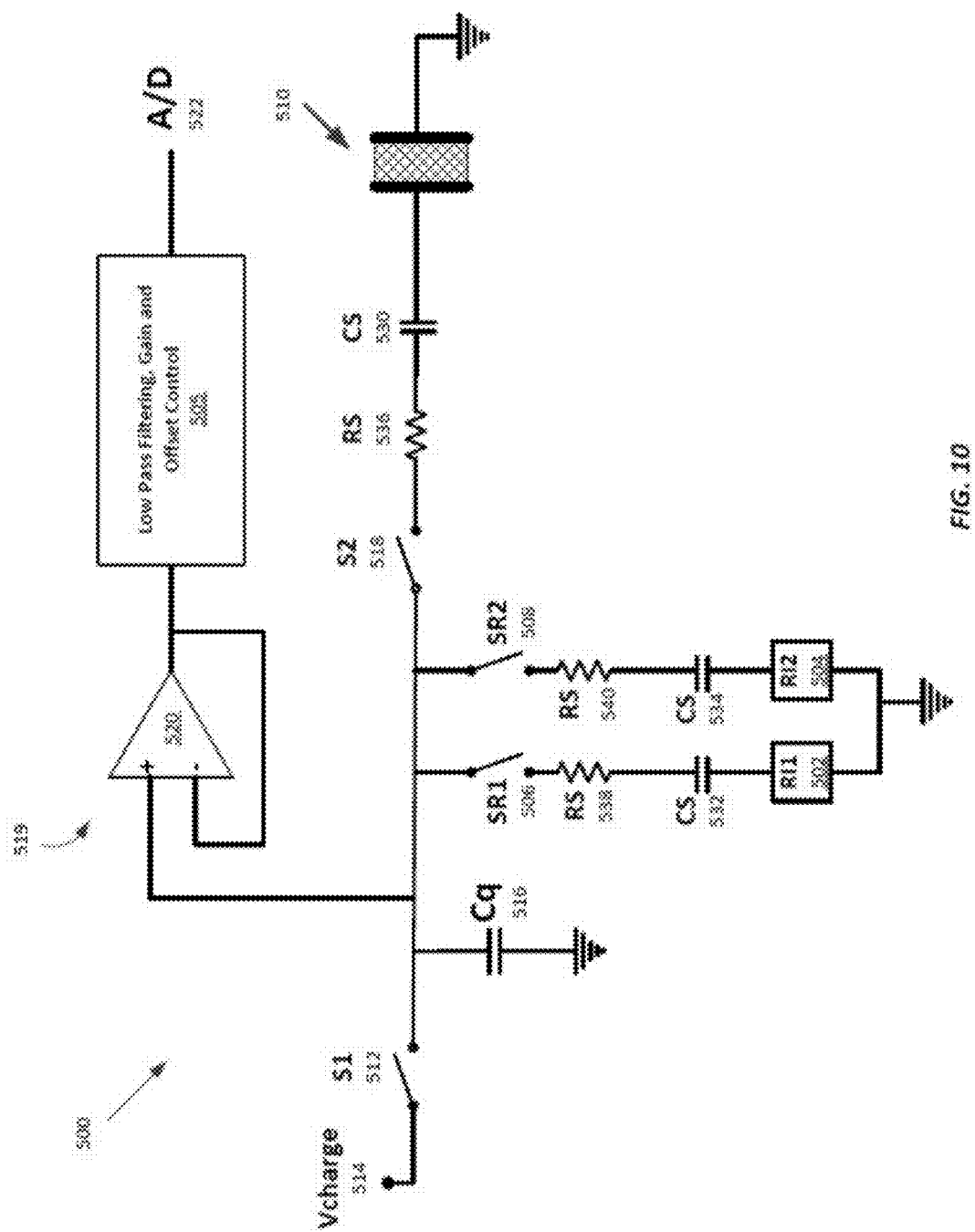
FIG. 10 illustrates another embodiment of the capacitive sensor system including additional passive components.

FIG. 10 shows a system with additional passive components to reduce electromagnetic interference, electrostatic discharge, and/or charge leakage susceptibility. Similar to FIG. 9, FIG. 10 illustrates a capacitive sensory system 500 using reference impedances RI1 502 and RI2 504 along with a low pass filter and/or gain and offset control 505 for signal conditioning, but also includes additional passive components. The reference impedances 502 and 504 are connected to the voltage measurement circuit via additional charge transfer switches SR1 506 and SR2 508. The capacitive sensory system 500 of FIG. 10 also includes components similar to the capacitive sensory system 100 shown and described in relation to FIG. 1. The capacitive sensory system includes a measurement cell 510 (or sensor), a first switch (S1) 512, a power source or voltage source (Vcharge) 514, a charging capacitor (Cq) 516, a second switch (S2) 518, and a voltage measurement circuit 519 that includes an op amp 520, a signal conditioning block 505, and an A/D converter 522. The current path that includes switches S2 518, SR1 506, and SR2 508 also include passive components, such as capacitors 530, 532, and 534 and resistors 536, 538, and 540, respectively. Resistor 536 and capacitor 530 are located in series with S2 518 between S2 518 and the measurement cell 510. Similarly, resistor 538 and capacitor 532 are located in series with SR1 506 between SR1 506 and the reference impedance RI1 502, and resistor 540 and capacitor 534 are located in series with SR2 508 between SR2 508 and the reference impedance RI2 504.

To reduce problems with electromagnetic interference, electrostatic discharge, or charge leakage through the transfer switches, passive components (e.g., capacitors 530, 532, and 534 and resistors 536, 538, and 540) are included along the charge transfer path between Cq 516 and measurement cell 510 and between Cq 516 and the reference impedances RI1 502 and RI2 504. For example, resistors 536, 538, and 540 are placed in series with the switches 518, 506, and 508 to reduce electrostatic discharge susceptibility. Transient voltage suppressors, diodes, or other protection circuitry can also be connected to the nodes of the sensor cell or measurement cell 510 and the reference impedances RI1 502 and RI2 504. For optimum measurement accuracy, the path to the measurement cell 510 and the reference impedances 502 and 504 also include the additional resistance and capacitance represented by resistors 536, 538, and 540 and capacitors 530, 532, and 534, respectively. Similar to Equation 9 above, a calculated value for the capacitance across the measurement cell (i.e., CLfinal) can be determined with known capacitance values for capacitors 530, 532, and 534. Similarly, a calculated value for the resistance across the measurement cell (i.e., RLfinal) can be determined with known resistance values for resistors 536, 538, and 540.

Electromagnetic noise is also a concern for measurement systems. Electromagnetic noise occurs in a broadband measurement, such as when using charge transfer measurement techniques. The averaging of measurements can be used to eliminate random noise as long as measurements do not become non-linear. In this case, averaging can be performed by taking multiple separate measurements and averaging the results in software. A different method of averaging is also possible using a "burst" of closures of the charge transfer switches S2 518, SR1 506, and SR2 508. Using the "burst" method of closures effectively performs the averaging in hardware.

For example, instead of closing S2 518 for one 100 ns period, S2 will be closed multiple separate times (i.e., a burst of times) each for 100 ns without recharging Cq 516. In this example, Cq 516 is much larger than the sensor capacitance (CL 132 of FIG. 3). Depending on the number of charge transfers within a burst, the capacitance of Cq 516 may be more than 1000 times the approximate value of the sensor capacitance (CL 132 of FIG. 3).

The sensor capacitance should be discharged between charge transfers, including the charge transfer times within the burst. Thus, enough time should occur between each of the charge transfer times within the burst for the sensor capacitance to discharge completely. If the sensor resistance RL (134 of FIG. 3) is relatively low (e.g., less than 1000Ω), the sensor capacitance will be discharged in a short time period (e.g., five times the RC time constant of the sensor capacitance CL and the sensor resistance RL). For example, if the sensor capacitance CL is about 10 pF and the sensor resistance RL is about 1000Ω, the sensor capacitance discharges in about 50 ns after S2 518 is opened. Thus, a time delay between transfer times of about 1 μs is sufficient for the sensor capacitance to completely discharge with a 50 ns discharge value. Higher values of sensor capacitance and/or sensor resistance might use larger delays between charge transfer periods. If helpful, an additional switch (not shown) can be used to short the sensor to ground between the transfer times to ensure that the sensor capacitance is discharged.

The information obtained by closing the charge transfer switch S2 once for 100 ns (e.g., using a small value for Cq) may not be the same as the information obtained by a burst of multiple (e.g., 100) switch closures of S2 (using a much larger value of Cq). But, the information for multiple charge transfer switch closures is generally close enough to the information for a single charge transfer switch closure, so that the same calculations as outlined earlier (e.g., Equations 1-8) can be used with the burst technique with accurate results. The accuracy can also be improved when reference impedances and the associated compensation calculation are used, as shown and described in relation to FIGS. 8-10 (assuming the same burst strategy used to measure the measurement cell is also used to measure reference impedances).

Referring back to FIG. 1, the system using a transfer time burst strategy uses a modified sequence as described below. First, S2 118 is opened. Then S1 112 is closed, which charges the capacitor Cq 116 until Cq 116 has a voltage of Vcharge 114. Next, S1 is opened, and a measurement of the voltage on Cq 116 is made using the A/D converter 122 of the microprocessor. A charge transfer burst counter is initialized to zero. S2 118 is closed for a short "charge transfer time," such as 100 ns, and the charge transfer burst counter is incremented for each pulse of the burst. Then S2 118 is opened. The system delays just long enough for the sensor capacitance of the measurement cell 110 to discharge. The charge transfer burst counter is compared to a target number of transfer times in the burst (e.g., 100). If the target number of transfer times in the burst has not been met (i.e., the charge transfer burst counter is less than the target number of transfers times in the burst), S2 118 is closed for another short "charge transfer time," such as 100 ns, the charge transfer burst counter is incremented, and the process repeats. If the target number of transfer times in the burst has been met (i.e., the charge transfer burst counter is greater than or equal to the target number of transfers times in the burst), another measurement of the voltage on Cq 116 is made using the A/D converter 122 of a microprocessor with both S1 112 and S2 118 opened.

The process of opening S2 118, closing S1 112, opening S1 112, measuring the voltage on Cq 116, closing S2 118 and opening S2 118 for each pulse in burst mode, and measuring the voltage again on Cq 116 is repeated again, except in the second process a relatively larger charge transfer time is used, such as 200 ns.

Similar to the a single charge transfer switch closure process, the measurements are used to calculate: a) an RC time constant, b) the actual charge sent through S2 118 during the initial few nanoseconds after S2 118 was closed, c) the capacitance of the measurement cell 110, and d) the resistance across the measurement cell 110.

For processes having multiple charge transfer switch closures (pulses in the burst), a scaling factor is used in the calculations to account for the number of separate pulses in the burst. For example, Equation 7 is modified to calculate the capacitance CL, whereby the result from the above calculations (e.g., Equations 1-6) is divided by the number of pulses, as shown in Equation 10. Additionally, Equation 8 is modified to calculate the resistance RL, whereby the result is multiplied by the number of pulses, as shown in Equation 11.

$$CL = Q\text{transferred}/V3 \text{ ns/number of pulses} \qquad \text{[Equation 10]}$$

$$RL = \text{number of pulses} * RC/(Cq+CL) \qquad \text{[Equation 11]}$$

The above-described systems and methods can be used with many types of measurement cells. To make accurate measurements of the liquid's conductivity or dielectric constant, the volume and/or concentration of the fluid (or other material) sensed by measurement cell should be relatively constant between measurements. One method to keep the volume of the fluid relatively constant is to shield the volume of liquid in the measurement cell from additional liquid, or other material, outside the measurement cell.

Figure 11:
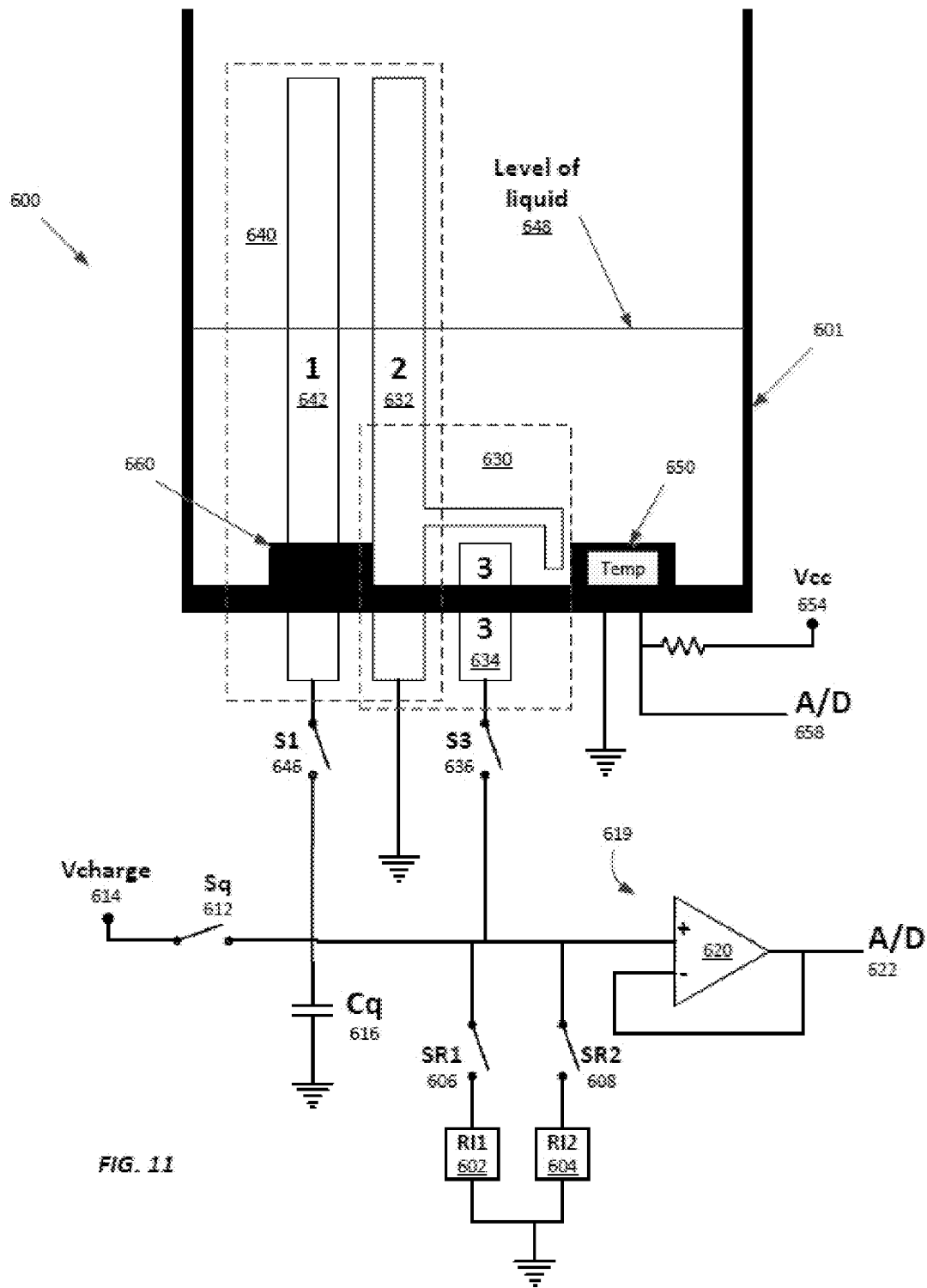
FIG. 11 illustrates the capacitive sensor system in a diesel exhaust fluid sensing system.

The measurement cells may be used for different fluid applications. For example, in a diesel exhaust fluid (DEF) application, a level sensor (fluid level sensor) may be integrated with a liquid quality sensor (fluid quality sensor). FIG. 11 illustrates a diagram of a system for an integrated fluid sensor.

Similar to FIG. 8, FIG. 11 illustrates a capacitive sensory system 600 used with a tank 601 for liquid (e.g., DEF) using reference impedances RI1 602 and RI2 604. The reference impedances 602 and 604 are connected to the voltage measurement circuit via additional charge transfer switches SR1 606 and SR2 608. The capacitive sensory system 600 of FIG. 11 also includes components and connections similar to the capacitive sensory system 100 shown and described in relation to FIG. 1. The capacitive sensory system includes a charging switch (Sq) 612, a power source or voltage source (Vcharge) 614, a charging capacitor (Cq) 616, and a voltage measurement circuit 619 that includes an op amp 620 and an A/D converter 622. The charging switch (Sq) 612 functions similar to S1 in FIGS. 1-2 and 8-10. The system includes two measurement cells. A quality measurement cell 630 (or quality sensor) is formed by electrode E2 632 and electrode E3 634. The quality measurement cell 630 is coupled to Cq 616 and the voltage measurement circuit 619 via the electrode E3 634 through a switch S3 636. A level measurement cell 640 (or level sensor) is formed by electrode E2 632 and electrode E1 642. The level measurement cell 640 is coupled to Cq 616 and the voltage measurement circuit 619 via the electrode E1 642 through a switch S1 646. The electrode E2 632 is coupled to a common voltage connection (e.g., ground voltage).

The tank 601 is configured for a liquid or fluid (e.g., DEF) with a variable level of liquid 648. The tank 601 also includes a temperature sensor 650. A first terminal of the temperature sensor 650 is coupled to a power supply voltage (Vcc) 654 via resistor and the second terminal is coupled to a common voltage connection (e.g., ground voltage). The first terminal (or output terminal) of the temperature sensor 650 is also coupled to an A/D converter 658. In some configurations, the system 600 uses the same A/D converter (e.g., 622 or 658) of a microprocessor to measure the measurement cells 630 and 640 and the temperature via the temperature sensor 650.

The sensing electrodes E1 642, 2632, and 3634 can be made of various conductors (or metals), such as a corrosion resistant stainless steel. Electrode E2 632 is grounded and is used as an electrode for the quality measurement cell 630 and the level measurement cell 640. The capacitance and resistance between electrodes E2 632 and 3 634 in the quality measurement cell 630 are used to assess the quality of the fluid that fills the volume between electrodes E2 632 and E3 634 above the bottom plate of the tank 601. The sensor capacitance and sensor resistance between electrodes E2 632 and E3 634 are calculated using one of the various processes described above. The measured capacitance and resistance can be compared to threshold values stored in memory to identify whether the fluid in the tank has an acceptable capacitance and resistance relative to a reference capacitance and resistance for the specified fluid.

The capacitance and resistance of a fluid can change with temperature. The tank also includes a temperature sensor 650 to detect this change in temperature. The temperature sensor 650 is used to modify the threshold values against which the calculated liquid properties (e.g., capacitance and resistance) are compared. For example, at 80° Celsius (C), the dielectric constant of a water based liquid is lower than the same liquid at 20° C. The temperature sensor 650 can use a thermistor or another method of determining the temperature near the quality sensor. For better accuracy and compensation for temperature, the temperature sensor is placed close to the volume of the quality measurement cell 630.

The level of the fluid is calculated by calculating the ratio of the capacitance between electrodes E1 642 and 2 632 in the level measurement cell 640 over the capacitance between electrodes E2 632 and 3 634 in the quality measurement cell 630 (assuming that the fluid completely fills the gap between electrodes E2 632 and E3 634 and surrounding area impacting a capacitance measurement). As the level increases, that capacitance ratio increases. Alternately, the ratio of the resistance between electrodes E2 632 and E3 634 over the resistance between electrodes E1 642 and E2 632 can also be used as an indicator of the liquid level. The sensor capacitance and sensor resistance between electrodes E1 642 and E2 632 are calculated using one of the various processes described above.

A bottom insulator plate 660 is partially covering the bottom of the electrode E1 642 above the bottom of the tank 601. The bottom insulator plate 660 adds capacitance so that the capacitance between electrodes E1 642 and E2 632 increases slowly at low liquid levels. The bottom insulator plate 660 makes the capacitance level ratio very small until the liquid level reaches above the bottom insulator plate 660 at the base of electrode E1 642.

Like most capacitive sensing systems, it is generally advantageous to mount the sensing electronics as close to the sensing electrodes as possible. Having sensing electronics (e.g., voltage measurement circuit) in close proximity to the sensing electrodes (e.g., measurement cell) minimizes the parasitic capacitances, and also minimizes the series inductance between Cq and the sensing electrode.

Figure 12:
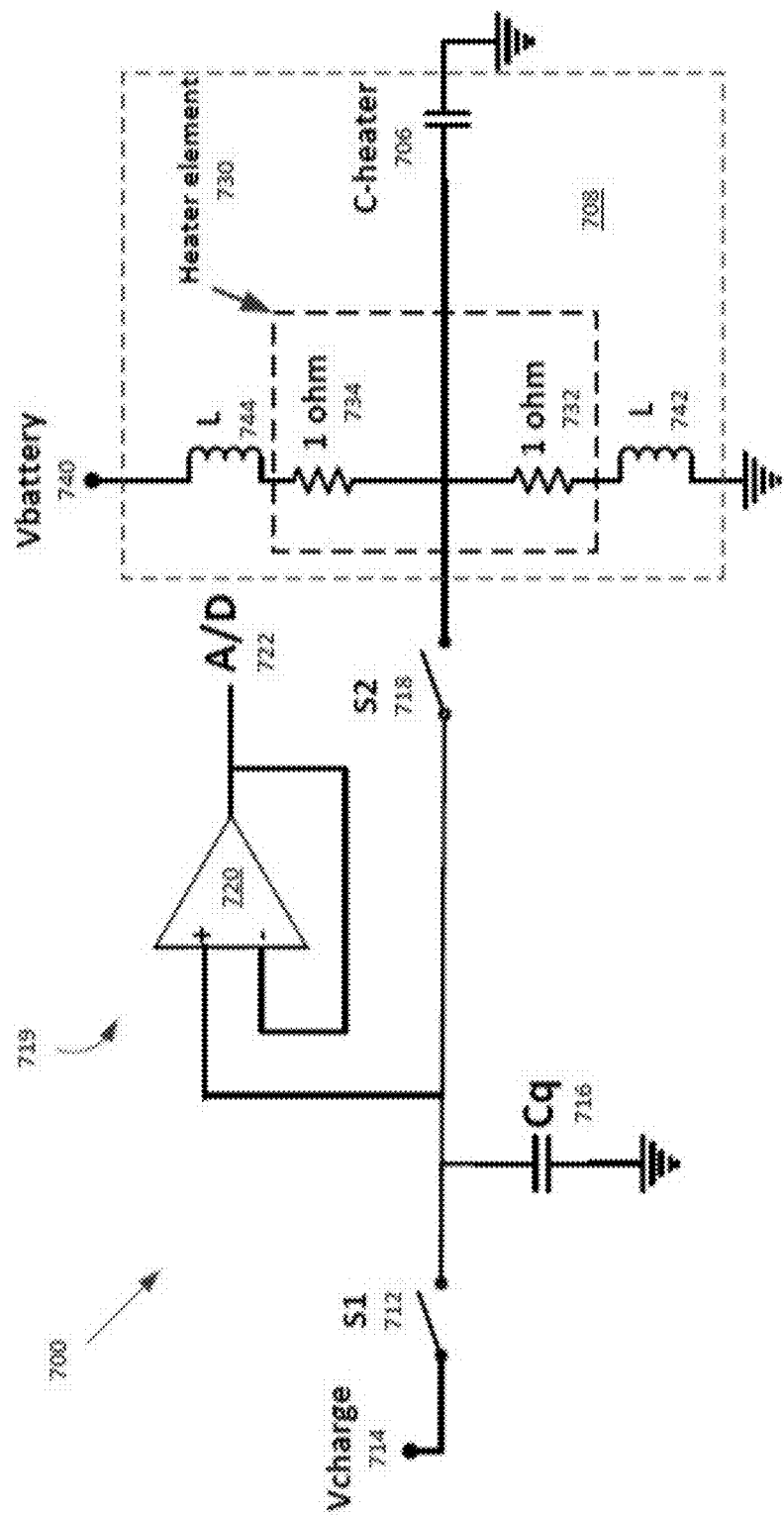
FIGS. 12-13 illustrate the capacitive sensor system used with a heater.
Figure 13:
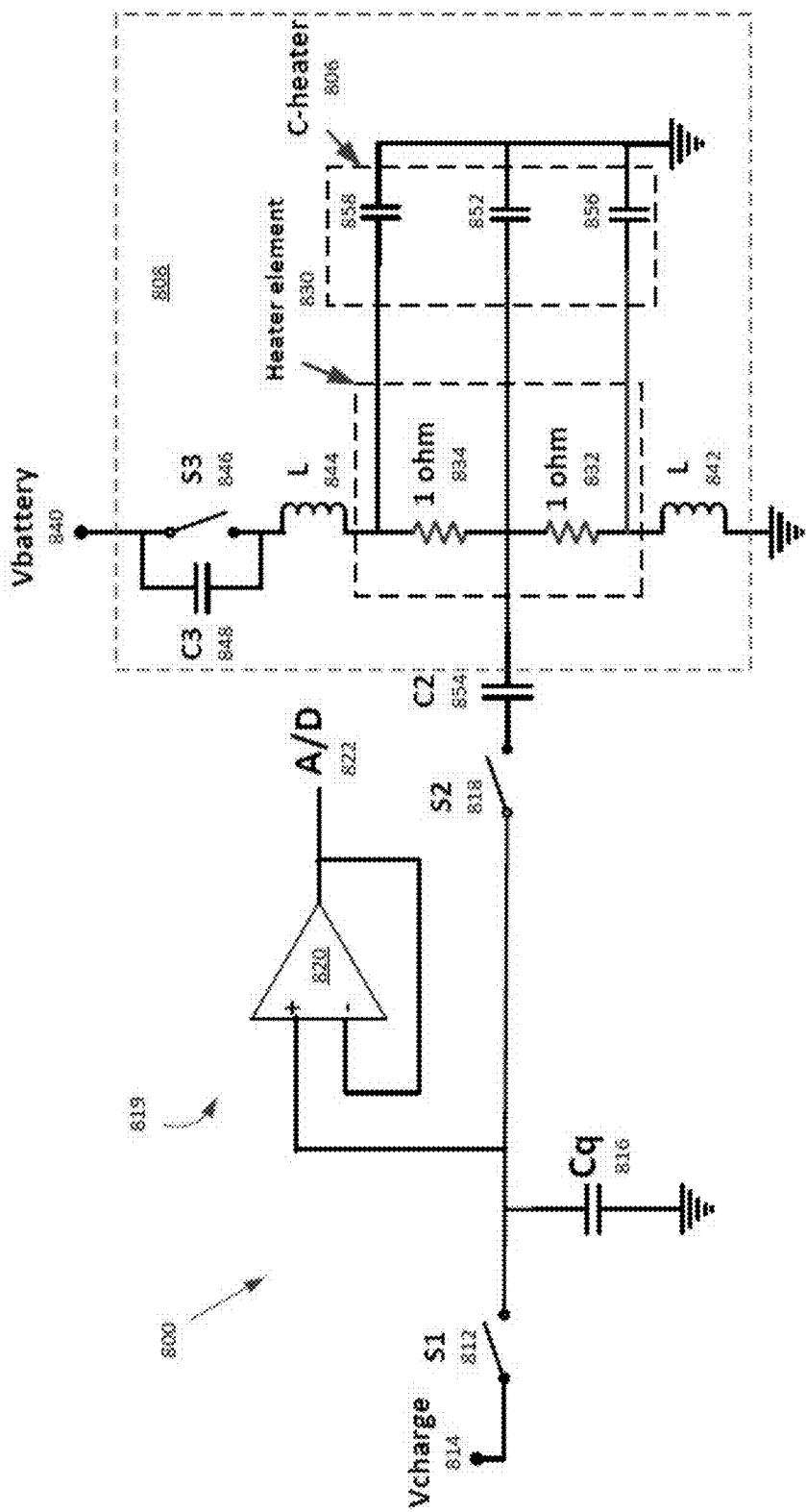

Capacitive measurement systems described may also be used to measure capacitance without using a liquid between the at least two conducting electrodes. For example, FIGS. 12-13 illustrate capacitive measurement systems used with a heater. FIG. 12 illustrates a capacitive measurement system 700 with a sensor capacitance (C-heater) 706 for a heater 708 that functions similar to a measurement cell (shown in FIGS. 1-2). The capacitive measurement system 700 of FIG. 12 also includes components and connections similar to the capacitive sensory system 100 shown and described in relation to FIG. 1. The capacitive measurement system 700 includes a first switch (S1) 712, a power source or voltage source (Vcharge) 714, a charging capacitor (Cq) 716, a second switch (S2) 718, and a voltage measurement circuit 719 that includes an op amp 720 and an A/D converter 722. The heater 708 also includes a heater element 730 represented by two 1 S2 resistors 732 and 734. The C-heater 706 represents the capacitance from the heater to ground and is the capacitance to be measured. The different capacitance measured on C-heater can be used to identify the occupant type sitting in the seat (e.g. an adult or a child seat). The heater element 730 is coupled to common connection (e.g., ground) via a first inductor 742 and coupled to a battery source (Vbattery) 740 via a second inductor 744.

The inductors 742 and 744 are added outside the heater's resistor circuit 730 to increase the impedance to high frequency current flow to the low impedance voltages sources (battery and ground). Thus, when S2 718 is closed, a fast charge transfer to C-heater 706 occurs, and the discharge of Cq 716 and C-heater 706 is much slower.

FIG. 13 illustrates a capacitive measurement system 800 with sensor capacitance, C-heater 806, represented as three parallel capacitors. The three parallel capacitors shows distributed capacitance across the whole heater 808 (assuming the high frequency heater impedance is very small compared to the high frequency impedance of the inductors).

The capacitive measurement system 800 of FIG. 13 also includes components and connections similar to the capacitive sensory system 100 shown and described in relation to FIG. 1. The capacitive measurement system 800 includes a first switch (S1) 812, a power source or voltage source (Vcharge) 814, a charging capacitor (Cq) 816, a second switch (S2) 818, and a voltage measurement circuit 819 that includes an op amp 820 and an A/D converter 822. The heater 808 also includes a heater element 830 represented by two 1 S2 resistors 832 and 834 in series. A first resistor 832 of the heater element 830 is coupled to the common connection (e.g., ground) via a first inductor 842. A second resistor 834 of the of the heater element 830 is coupled to a battery source (Vbattery) 840 via a second inductor 844 in series with switch S3 846 in parallel with capacitor C3 848. A first terminal of the two 1Ω resistors 832 and 834 is coupled to a terminal of a first capacitor 852 of the C-heater 806 and S2 818 via capacitor C2 854. Capacitor C2 854 provides DC isolation between the measurement circuit and the heating circuit, so the battery has minimal impact on the measurements taken by the measurement circuit. A second terminal of the first resistor 832 is coupled to a terminal of the second capacitor 856 of the C-heater 806. A second terminal of the second resistor 834 is coupled to a terminal of the third capacitor 858 of the C-heater 806. Another terminal of each of the capacitors 852, 856, and 858 is coupled to the common connection (e.g., ground).

The inherent sensor capacitance, C-heater 806, is shown as three parallel capacitors 852, 856, and 858 to illustrate that a distributed capacitance occurs across the whole heater (again assuming the high frequency heater impedance is very small compared to the high frequency impedance of the inductors). With the selected S2 closure times (charge transfer times) or sampling of the Cq 816, the charge transferred to C-heater 806 can be identified using the techniques and equations provided above.

The switch S3 846 that controls the current to the heater 808 is open when a measurement is made such that the nodes in heater are at the same potential. The capacitor C3 848 is in parallel with S3 846. In some applications, the switch S3 846 is actually a transistor having an intrinsic parallel capacitance across S3 846, represented as C3 848. This parallel capacitor C3 848 can make the capacitance measurements more difficult with a heater because a large offset capacitance occurs from the heater 808 directly to battery or ground. With sufficiently short charge transfer times (e.g., possible less than 10 ns), the measurement system 800 allows C-heater to be measured directly.

When the heater 708 and 808 is a seat heater for a vehicle, the measurement of C-heater 706 and 806 of the seat heater element can be used to identify whether an adult or a child seat is in the front passenger seat of a vehicle. The information from these measurements can then be used to determine whether to deploy an airbag (e.g., a passenger side airbag). When the heater 708 and 808 is a steering wheel heater for a vehicle, the measurement of C-heater 706 and 806 of a steering wheel heater can be used to identify if the driver's hands are on the wheel. The information from these measurements can be used when the vehicle determines to autonomously turn the steering wheel during vehicle self-park situations.

Reference impedances (e.g., shown in FIGS. 8-10) can also be used when making capacitance measurements using a heater (e.g., shown in FIGS. 12-13).

Figure 14:
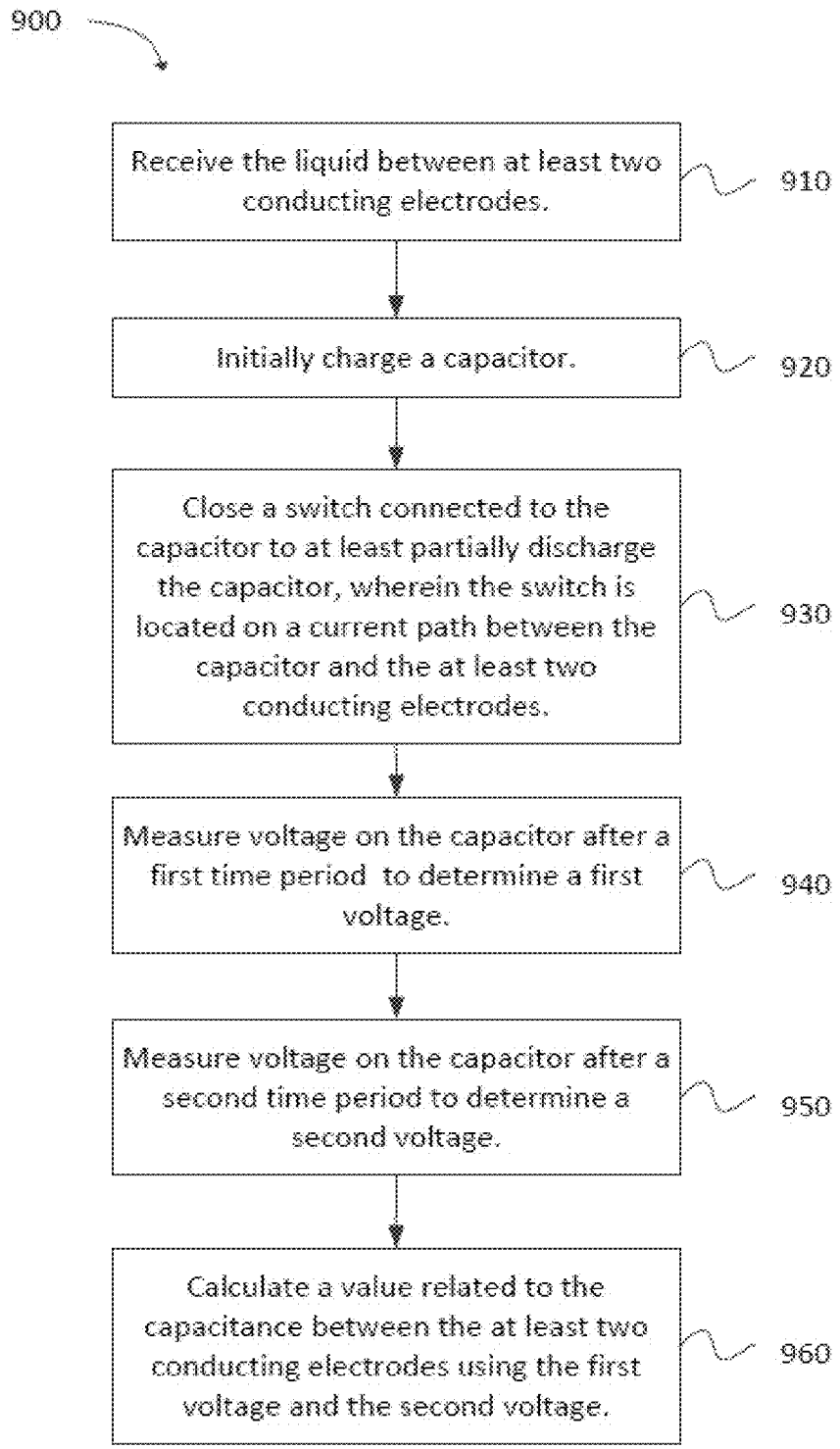
FIG. 14 illustrates a flowchart of an exemplary process of measuring a property of a liquid using a liquid property measurement system.

Another exemplary method, method 900, is illustrated in FIG. 14. The method 900 includes a process of measuring a property of a liquid using a liquid property measurement system. The method 900 may be carried out by, for example, one of the systems 100, 126, 300, 400, 500, or 600 described above. The method begins by receiving the liquid between at least two conducting electrodes, as in block 910. The second step includes initially charging a capacitor, as in block 920. The next step can include measuring an initial voltage on the capacitor. The next step includes closing a switch connected to the capacitor to at least partially discharge the capacitor, as in block 930. The switch is located on a current path between the capacitor and the at least two conducting electrodes. Another step includes measuring voltage on the capacitor after a first time period to determine a second voltage, as in block 940. The process can repeat to discharge the capacitor for a second time period that is different (e.g., shorter or longer) than the first time period. More particularly, the method can continue by charging the capacitor again. The next step may include closing the switch to at least partially discharge the capacitor. Then, the voltage is measured on the capacitor after a second time period to determine a third voltage, as in block 950. Next, a value is calculated related to the capacitance between the at least two conducting electrodes using the first voltage and second voltage, as in block 960. The initial voltage can also be used to calculate the value related to the capacitance between the at least two conducting electrodes.

The calculated capacitance can be used to determine the dielectric constant of the liquid, as previously described. The method can further include calculating a second value related to the resistance between the at least two conducting electrodes using the first voltage and the second voltage. The calculated resistance can be used to determine conductivity of the liquid, as previously described. The two conductors can be part of a measurement cell.

Although the microprocessor 123 is only shown in FIG. 1, a similar microprocessor may be included in the other embodiments discussed herein, including systems 126, 300, 400, 500, 600, 700, and 800, for carrying out similar functions (e.g., processing measurement data and controlling switches).

Thus, the invention provides, among other things, systems and methods for making repeatable measurements of the dielectric constant and conductivity of a material, such as a liquid.

While the forgoing examples are illustrative of the principles of the present invention in one or more particular applications, it will be apparent to those of ordinary skill in the art that numerous modifications in form, usage and details of implementation can be made without departing from the principles and concepts of the invention. Accordingly, it is not intended that the invention be limited, except as by the claims set forth below.

What is claimed is:

1. A liquid property measurement system comprising:
a measurement cell having at least two conducting electrodes configured to receive a liquid between the at least two conducting electrodes;
a capacitor;
a voltage measurement circuit configured to determine a voltage on the capacitor;
a first switch coupled to the capacitor and in a current path between the capacitor and a voltage source; and
a second switch coupled to the capacitor and in a current path between the capacitor and the measurement cell,
wherein
the first switch is initially open,
the first switch is then closed to initially charge the capacitor and then opened, and a voltage on the capacitor is determined for an initial voltage measurement,
after the first switch is opened, the second switch is closed for a first time period and then the voltage on the capacitor is determined for a first voltage measurement,
the first switch is then closed to charge the capacitor again and then opened,
after the first switch is opened, the second switch is closed for a second time period and then the voltage on the capacitor is determined for a second voltage measurement, and
using the initial voltage measurement, the first voltage measurement, and the second voltage measurement, a value is calculated related to the capacitance between the at least two conducting electrodes of the measurement cell.

2. The system of claim 1, further comprising:
at least one reference impedance component;
at least one reference switch selectively coupling the reference impedance component to the capacitor;
wherein
the first switch is closed to charge the capacitor and then opened,
after the first switch is opened, the at least one reference switch is closed for the first time period and then the voltage on the capacitor is determined for a first reference impedance voltage measurement,
the first switch is then closed to charge the capacitor again and then opened,
after the first switch is opened, the at least one reference switch is closed for the second time period and then the voltage on the capacitor is determined for a second reference impedance voltage measurement, and
using the first reference impedance voltage measurement and the second reference impedance voltage measurement, a reference value is calculated related to the impedance of the at least one reference impedance component,
using the value and the reference value, a compensated value is calculated related to the capacitance between the at least two conducting electrodes of the measurement cell.

3. The system of claim 2, wherein the at least one reference impedance component includes at least one selected from the group consisting of a capacitor and a resistor.

4. The system of claim 1, further comprising:
a tank configured to contain the liquid,
wherein the at least two conducting electrodes form a fluid quality sensor and the measurement cell includes at least one further conducting electrode forming a fluid level sensor with one of the at least two conducting electrodes.

5. A method of measuring a property of a liquid using a liquid property measurement system, the method comprising:
receiving the liquid between at least two conducting electrodes;
initially charging a capacitor;
determining an initial voltage on the capacitor;
closing a switch connected to the capacitor to at least partially discharge the capacitor, wherein the switch is located on a current path between the capacitor and the at least two conducting electrodes;
determining voltage on the capacitor after closing the switch to discharge the capacitor for a first time period to determine a first voltage;
charging the capacitor again;
determining voltage on the capacitor after closing the switch to discharge the capacitor for a second time period to determine a second voltage, wherein the first time period is a different length of time than the second time period; and
calculating a value related to an impedance between the at least two conducting electrodes using the initial voltage, the first voltage and the second voltage.

6. The method of claim 5, wherein the value is one of a dielectric constant and a conductivity of the liquid.

7. The method of claim 5, wherein the impedance includes at least one selected from the group consisting of capacitance and resistance.

8. The method of claim 5, wherein charging the capacitor is accomplished by temporarily closing a first switch to connect the capacitor to a power source.

9. A capacitance measurement system comprising:
a measurement cell having at least two conducting elements;
a capacitor;
a voltage measurement circuit configured to measure a voltage on the capacitor;
a switch coupled to the capacitor and in a current path between the capacitor and the measurement cell,
wherein
the switch is initially open,
the capacitor is initially charged and the voltage on the capacitor is measured for an initial voltage measurement,
the switch is closed,
after a first time period the voltage on the capacitor is measured for a first voltage measurement, and
after a second time period the voltage on the capacitor is measured for a second voltage measurement, and
using the initial voltage measurement, the first voltage measurement, and the second voltage measurement, a value is calculated related to the capacitance between the at least two conducting elements of the measurement cell.

10. The system of claim 9, wherein the value is used to calculate a second value that is related to the dielectric constant of the liquid.

11. The system of claim 9, wherein the first time period and the second time period represent the periodic sampling of the capacitor for the first voltage measurement and the second voltage measurement.

12. The system of claim 9, further comprising:
a power source; and
a resistor coupled between the power source and capacitor to initially charge the capacitor.

13. The system of claim 9, further comprising:
a power source; and
a charging switch coupled between the power source and capacitor to initially charge the capacitor.

14. The system of claim 9, wherein after the voltage on the capacitor is measured for the first voltage measurement the capacitor is charged again, and then the voltage on the capacitor is measured for the second voltage measurement.

15. A capacitance measurement system comprising:
a measurement cell having at least two conducting elements;
a capacitor;
a voltage measurement circuit configured to measure a voltage on the capacitor;
a switch coupled to the capacitor and in a current path between the capacitor and the measurement cell;
a microprocessor configured to execute instructions that use a plurality of voltage measurements on the capacitor to calculate a value related to the charge sent through the switch to the measurement cell,
wherein the charge sent through the switch to charge the measurement cell is used to calculate a value related to the capacitance between the two conducting elements of the measurement cell.

16. The system of claim 15, further comprising resistive element coupled between the conducting elements.

17. The system in claim 16 where the calculated charge sent through the switch to charge the measurement cell excludes the current that heats the resistive element.

18. The system of claim 15, wherein:
the switch is initially open, and
the capacitor is initially charged and the voltage on the capacitor is measured for an initial voltage measurement, and
the value is calculated related to the capacitance between the at least two conducting elements of the measurement cell using the initial voltage measurement, the first voltage measurement, and the second voltage measurement.

* * * * *